United States Patent [19]
Takahashi et al.

[11] Patent Number: 5,735,793
[45] Date of Patent: Apr. 7, 1998

[54] ENDOSCOPE

[75] Inventors: Yukio Takahashi, Hachioji; Ichiro Nakamura, Kokubunji; Masaaki Nakazawa, Hachioji; Hideo Ito, Akishima; Hisao Yabe, Hachioji, all of Japan

[73] Assignee: Olympus Optical Co., Ltd., Tokyo, Japan

[21] Appl. No.: 678,180

[22] Filed: Jul. 11, 1996

Related U.S. Application Data

[63] Continuation-in-part of Ser. No. 585,315, Jan. 11, 1996, abandoned.

[30] Foreign Application Priority Data

Jan. 12, 1995 [JP] Japan .................................. 7-3585
Sep. 12, 1995 [JP] Japan .................................. 7-234486

[51] Int. Cl.⁶ .................................................. A61B 1/00
[52] U.S. Cl. ............................................. 600/153; 600/104
[58] Field of Search .................................... 600/104, 153, 600/154, 156, 157, 158, 159; 138/118, 120, 137, 140; 403/185, 202, 220, 405.1

[56] References Cited

U.S. PATENT DOCUMENTS 4,967,732  11/1990  Inoue ............................... 600/153 X

FOREIGN PATENT DOCUMENTS 5-20706  3/1993  Japan.

*Primary Examiner*—Beverly M. Flanagan
*Attorney, Agent, or Firm*—Morgan, Lewis & Bockius LLP

[57] ABSTRACT

An endoscope having a conduit-providing flexible tube and a device for connecting said flexible tube, said device comprising a coupling member that is provided on the outer circumference with a first tapered portion the outside diameter of which decreases toward at least one end of said coupling member and that has a conduit in the interior, an annular retaining member that is fitted over the outer circumference of one end portion of said flexible tube which is to be fitted over said first tapered portion and that has on the inner circumference a second tapered portion the inside diameter of which decreases toward said at least one end in such a way as to provide engagement with said first tapered portion, and a clamp member that depresses said retaining member in the axial direction in which said first tapered portion flares, thereby depressing said flexible tube to be secured to said coupling member, characterized by further having an urging and covering member that not only covers the outer circumferential portion of said flexible tube that has been fitted into said coupling member at the end portion coupled to said flexible tube but also urges said flexible tube to be secured to said first tapered portion.

29 Claims, 12 Drawing Sheets

5,735,793

1

ENDOSCOPE

This is a continuation-in-part of application Ser. No. 08/585,315, filed on Jan. 11, 1996, now abandoned.

BACKGROUND OF THE INVENTION

1. Field of the Invention

The present invention relates to an endoscope having a mechanism for coupling a flexible tube and other components.

2. Related Art

Endoscopes comprise two basic parts, an insertion section and a manipulating section coupled to the insertion section. Endoscopes also have channels through which medical devices are to be inserted, channels for the passage of fluids, as well as suction and other conduits. Having such many components, endoscopes are furnished with not only a mechanism for coupling the insertion and manipulating sections but also areas for connecting the various channels and conduits. While several design are known for providing such coupling mechanism and connecting areas, Unexamined Published Japanese Utility Model Application (kokai) Hei 5-20706 teaches a device for assuring positive fixation of a flexible tube in an endoscope. The device will now be explained briefly with reference to FIG. 14.

The endoscope described in this reference has a socket member 301 (coupling member) in the manipulating section and its body 302 has at the front end a mating portion 304 which is to be covered with a flexible tube 303. The outer circumference of the mating portion 304 is provided with a first tapered surface 305 the outside diameter of which increases progressively from the front to the rear end. A disk-shaped projection 306 is provided midway of the socket member 301 and an external thread portion 307 is formed on the outer circumference of the projection 306.

The external thread portion 307 is adapted to have threadable engagement with a fixing member 308 for holding the flexible tube 303 in position. To this end, the fixing member 308 is provided with an internal thread portion (clamp portion) 309 on the inner circumference at one end of the body which is generally in a hollow cylindrical form. The fixing member 308 has an inwardly bent flange portion 310 provided at the other end of its body.

The body of the fixing member 308 contains a retainer ring (retaining portion) 311 that holds the outer circumference of the coupling end portion of the flexible tube 303 fitted over the first tapered surface 305 around the mating portion 304 of the socket member 301. The inner circumference of the retainer ring 311 is provided with a second tapered surface 312 the inside diameter of which increases progressively from the flange portion 310 toward the internal threaded portion 309 of the fixing member 308.

In the design just described above, the angle $\theta_1$ of the first tapered surface 305 is set to be smaller than the angle $\theta_2$ of the second tapered surface 312 ($\theta_1 < \theta_2$).

The endoscope described in Unexamined Published Japanese Utility Model application (kokai) Hei-5-20706, supra, satisfies the relationship $\theta_1 < \theta_2$, so when the flexible tube 303 is to be secured to the mating portion 304 of the socket member 301, the tube will be clamped by the retainer ring 311 at the smaller-diameter end portion of the second tapered surface 312, with the clamp force being exerted on the area near the distal end of the first tapered surface 305 of the mating portion 304.

However, being thin and low in rigidity, the distal end portion of the first tapered surface 305 may deform when the flexible tube 303 is clamped. If such a deformation occurs, a gap forms between the flexible tube 303 and the mating portion 304 and filthy matter that collects in the gap under suction will inevitably prolong the cleaning time.

If a great bending force is exerted on the flexible tube 303, it may break in an area that contacts the front end portion of the socket member 301 or it may separate therefrom to produce a gap, in which filthy matter will collect and prolongs the cleaning time.

SUMMARY OF THE INVENTION

The present invention has been accomplished under these circumstances and has as an object providing an endoscope that has sufficient rigidity to permit coupling of a flexible tube without deformation thereby assuring positive fixation of the tube and that can be cleaned with higher efficiency in the absence of gaps that would otherwise be created in the portion of coupling to the tube and in which filthy matter will easily collect.

This object of the invention can be attained by an endoscope having a conduit-providing flexible tube and a device for connecting said flexible tube, said device comprising a coupling member that is provided on the outer circumference with a first tapered portion the outside diameter of which decreases toward at least one end of said coupling member and that has a conduit in the interior, an annular retaining member that is fitted over the outer circumference of one end portion of said flexible tube which is to be fitted over said first tapered portion and that has on the inner circumference a second tapered portion the inside diameter of which decreases toward said at least one end in such a way as to provide engagement with said first tapered portion, and a clamp member that depresses said retaining member in the axial direction in which said first tapered portion flares, thereby depressing said flexible tube to be secured to said coupling member, characterized by further having an urging and covering member that not only covers the outer circumferential portion of said flexible tube that has been fitted into said coupling member at the end portion coupled to said flexible tube but also urges said flexible tube to be secured to said first tapered portion.

In the flexible tube connecting device of the invention, the flexible tube is fitted around the coupling member in the first tapered portion the outside diameter of which decreases toward at least one end of said coupling member and the outer circumference of the tube is clamped with the clamp means so that said tube is secured to the coupling member; in addition, the urging and covering member not only covers the flexible tube also urges the inner circumference of the flexible tube against the fist tapered surface, thereby ensuring against the creation of filth-collecting gaps at the interface between the flexible tube and the first tapered surface.

DESCRIPTION OF THE PREFERRED EMBODIMENTS

Figure 1:
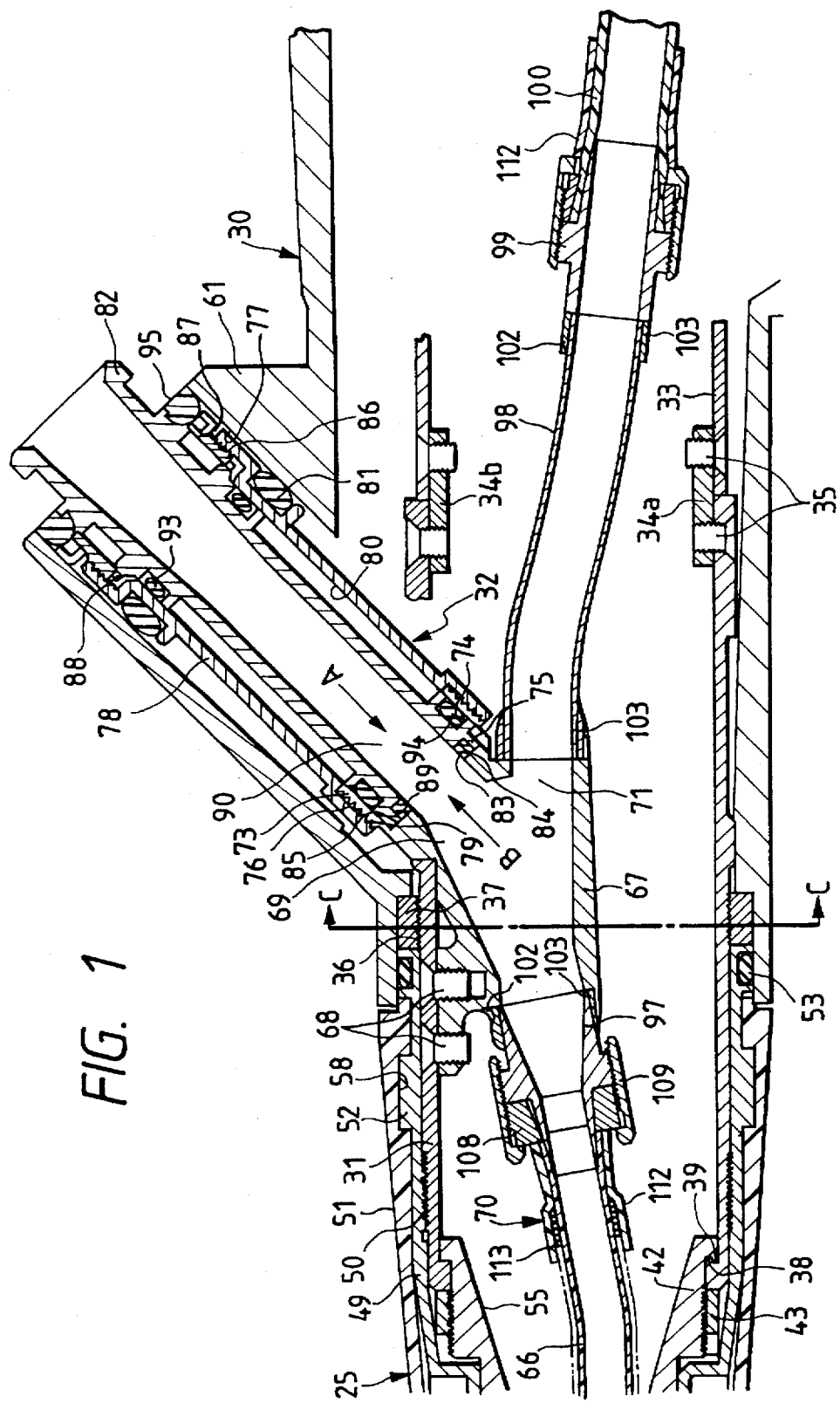
FIG. 1 is a longitudinal section of an area near the connection between the insertion and manipulating sections of an endoscope according to a first example of the invention.
Figure 2A:
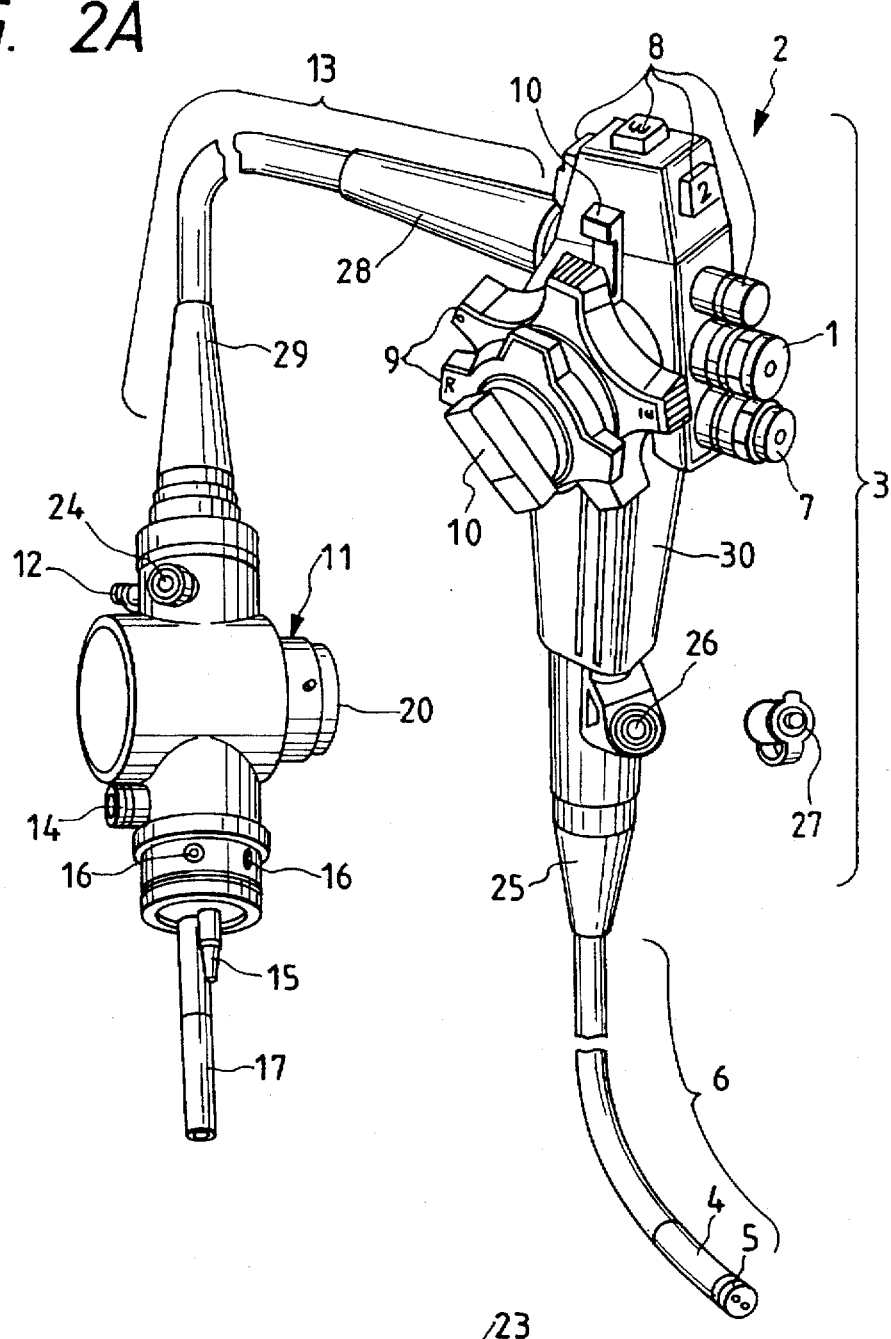
FIG. 2A shows the general appearance of the endoscope.
Figure 2B:
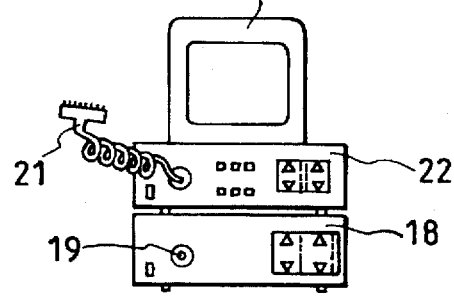
FIG. 2B is a front view of the equipment to be connected to the endoscope.
Figure 3:
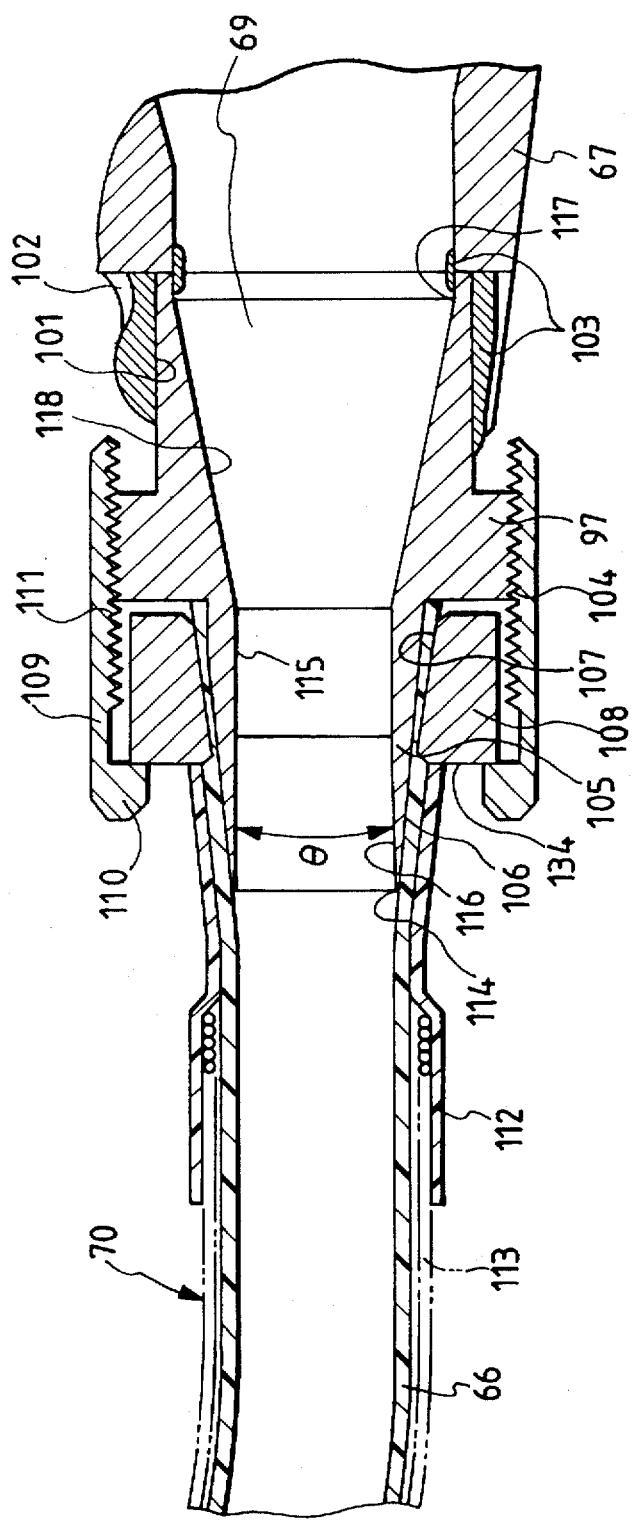
FIG. 3 shows in longitudinal section how the flexible tube and the bifurcate tube are each connected to the channel socket in the endoscope.

Four examples of the invention will now be described with reference to accompanying drawings. FIGS. 1, 2 and 3 show an endoscope according to the fist example of the invention. FIG. 1 is a longitudinal section of an area near the connection between the insertion and manipulating sections of the endoscope. FIG. 2A is a perspective view showing the general external appearance of the endoscope, and FIG. 2B is a front view of the equipment to be connected to the endoscope. FIG. 3 shows in longitudinal section how a flexible tube and a bifurcate tube are each connected to a channel socket member.

FIG. 2A shows the general appearance of the endoscope of the invention which is indicated by 2. As shown, the endoscope 2 comprises a manipulating section 3 close to the operator, a typically elongated insertion section 6 coupled to the manipulating section 3, and a universal cord 13 extending from a lateral side of the manipulating section 3.

The insertion section 6 which is covered with a resin such as polyurethane is connected at the rear end to the manipulating section 3 and the area of connection is protected with an anti-buckle portion 25. The insertion section 6 is curved in the front end 4 which is covered with a soft elastic material. The distal tip of the bending portion 4 has a rigid portion 5 that is provided with viewing optics facing an imaging device (not shown), illumination optics from which illuminating light will issue, as well as air/water supply nozzles, an exit for forceps, etc.

The manipulating section 3 is fitted with a suction control unit 1 to be used in applying suction, an air/water supply valve 7 to be manipulated for performing air/water supply, and remote switches 8 for processing picture signals delivered from an imaging device. The manipulating section 3 is also fitted with angle knobs 9 made of a hard resin and which are manipulated to move the bending portion 4 in both vertical and horizontal directions. The manipulation section is also fitted with two free engage (FE) levers 10 that are manipulated to either freeze the state of the bending portion 4 or free it from the curved state.

The universal cord 13 extending from the manipulating section 3 is covered with a resin such as polyurethane and fitted at the distal end with a connector 11 formed of a hard resin. The opposite ends of the universal cord 13, one being Connected to the manipulating section 3 and the other connected to the connector 11, are protected with buckle preventing members 28 and 29, respectively.

The connector 11 is provided with an S terminal 12 for returning a high-frequency leakage current to a cauterizer's power source, a metallic water supply socket 14 which is to be connected to a water supply tank (not shown) for supplying water, a metallic air-supply pipe 15, a metallic suction socket 24 which is to be connected to a suction pump (not shown), and a plurality of electric contacts.

The connector 11 is also provided with an end portion of a lightguide 17, which is to be connected to a connector receptacle 19 on a light source unit 18 (see FIG. 2B) to ensure illumination with light from the illumination optics in the rigid portion 5 at the distal tip of the insertion section.

The connector 11 also has an electric connector portion 20 on a lateral side. When this connector portion 20 is connected to a cord 21 extending from a video processor 22 as shown in FIG. 2B, the electric signal delivered from the imaging device can be visualized as a picture on the screen of a monitor 23.

The manipulating section 3 of the endoscope 2 is provided in the distal end portion with a grip 30 that is formed of a hard resin such as polysulfone and by which the operator can hold the endoscope 2. The grip 30 is provided on the lateral side with projecting port 26 through which a medical instrument such as forceps can be inserted. The port 26 is of such a design that a forceps plug 27 formed of an elastic material such as silicone rubber can be fitted thereto.

FIG. 1 is a sectional view of the part of the manipulating section 3 around the forceps insertion port 26.

The grip 30 of the endoscope 2 has incorporated therein an angle manipulating wire (not shown) in the form of a twisted strand of metal wires which is to be used for moving the bending portion 4 in a desired direction, an air and a water supply channel (not shown) which are formed of a fluororesin, and an electric cable (not shown) for transmitting output signals from the imaging device. These members are protected within a tubular member 31 that is slipped into the grip 30. Being made of an aluminum alloy, the tubular member 31 also serves to hold other members in position in the grip 30.

The tubular member 31 has an opening 32 formed in the area closer to the operator by cutting its top portion in an area extending from its right end to the central portion. The grip 30 also contains a metallic fixing frame 33 that is fixed to two metallic shims 34a by means of screws 35 and these shims are fixed to the open ends of the tubular member 31 by means of the screws 35. The shims 34b also serve to retain the rigidity of the tubular member 31 which would otherwise decrease in the presence of the opening 32.

The grip 30 is secured by tightening a metallic grip fixing ring 37 into engagement with a thread portion 36 that is provided around the center of the tubular member 31 in the axial direction.

The grip 30 is also provided with a projection 61 having the forceps insertion port 26. A recess is formed on both lateral sides of the projection 61 and three nameplates are fixedly bonded to the recesses. The first nameplate designates channel diameters and like information in a color different from the color of the second nameplate and is molded of a resin having that color. The second nameplate identifies the model of the endoscope and provides like information. The third nameplate identifies the name of the manufacturer and provides like information. The three nameplates are molded of a hard resin such as polysulfone.

The insertion section 6 of the endoscope 2 holds a flexible tube 66 in position that provides a channel 70 through which a medical instrument such as forceps can be inserted. An end of the flexible tube 66 is directed into the manipulating section 3 such that it communicates and connects to a bifurcate tube 67, which in turn is fixed to the tubular member 31 within the manipulating section 3 by means of screws 68. The bifurcate tube 67 has two conduits that are all formed by cutting. The channel 70 branches into two conduits 69 and 71 in the bifurcate tube 67; the conduit 69 is substantially linear and admits the passage of forceps and the conduit 71 is used to apply suction.

The bifurcate tube 67 has an end portion 73 positioned in a face-to-face relationship with a mounting hole 77 hat is made in the projection 61 from the grip 30 and which is oriented at an angle of 45 degrees with the length of the endoscope 2. The end portion 73 is formed on the side of the bifurcate tube 67 where the forceps conduit 69 runs. The end portion 73 has a thread portion 76 provided on the outer circumference and it also has a circular hole 74 of a greater diameter than the forceps conduit 69, as well as two members 75 for preventing rotation.

A connection cylinder 78 is inserted into the mounting hole 77 and an internal thread 79 at the lower end engages the external thread 76 on the bifurcate tube 67 to be fixed in contact with the end portion 73. The connection cylinder 78 has a circular bore 80 whose diameter is equal to or greater than the diameter of the circular hole 74. An O-ring 81 is fitted between the connection cylinder 78 and the mounting hole 77 to insure watertightness.

A tubular forceps socket 82 is inserted into the circular bore 80. A packing 83 molded of a hard and elastic resin such as silicone rubber is bonded to an end face 84 near the lower end of the forceps socket 82 by means of a silicone-base adhesive; the packing 83 is fitted into a circular hole 89 having a greater diameter than conduit 90 through the forceps socket 82 and the inside diameter of the packing 83 is substantially equal to the inside diameter of the forceps conduit 69 of the bifurcate tube 67. Thus, the conduit 90 through the forceps socket 82 can be connected to the forceps conduit 69 in such a way that their inner surfaces are substantially flush and have no steps formed thereon.

A retainer tube 87 is in threadable engagement with an internal thread portion 86 at the upper end of the connection cylinder 78 such that a flange 88 around the forceps socket 82 is depressed until the latter contacts an end face 85 near the end portion 73 of the bifurcate tube 67, whereupon the packing 83 is compressed and, at the same time, the forceps socket 82 is fixed to the bifurcate tube 67.

To insure watertightness, an O-ring 93 is fitted between the forceps socket 82 and the connection cylinder 78 and an O-ring 94 is fitted between the forceps socket 82 and the bifurcate tube 67. A cover member 95 molded of an elastic resin such as silicone rubbers is placed in contact with the upper end of the retainer tube 87, fitted into the mounting hole 77 and fixed in such a way that there is not step left at the joint with the projection 61 from the grip 30.

A channel socket 97 and a suction pipe 98 are soldered to the bifurcate tube 67; the flexible tube 66 providing the channel 70 is to be connected to the channel socket 97 and a suction socket 99 to be connected to the suction conduit 71 is connected to the suction pipe 98.

The suction pipe 98 is soldered to the suction socket 99 which, in turn, is connected to a suction tube 100 which, in turn, is connected to the suction control unit 1.

Since the coupling by soldering is identical in every soldered part, discussion will not be made only of the coupling between the channel socket 97 and the bifurcate tube 67.

As FIG. 3 shows, the bifurcate tube 67 has a hole 101 through which the channel socket 97 is to be fitted and at least one cutout 102 which is substantially equal in depth to the hole 101.

The channel socket 97 is fitted into the hole 101 and brought into contact with its end face to achieve coupling. The inside diameter of the forceps conduit 69 is substantially equal to the inside diameter of the bore 117 at the rear end of the channel socket 97; at the joint between the two members, a layer of solder or adhesive 103 extends to bridge them so that they provide substantially equal inside diameters to form a continuous conduit.

The channel socket 97 has a large-diameter external thread portion 104 midway of its length, as well as a small-diameter mating portion 105 that is formed at the distal end and over which the flexible tube 66 is to be fitted. The outer circumference of the mating portion 105 has a first tapered portion 106 the diameter of which increases progressively from the front end 114 toward the rear end.

The flexible tube 66 is fitted over the first tapered portion 106 and bonded thereto. A retainer ring 108 is fitted over the outer circumference of the flexible tube 66 and the inner circumference of the ring has a second tapered surface 107 which flares progressively from the front end 134 toward the rear end. A flange portion 110 provided inwardly at the front end of a fixing member 109 contacts the surface of the front end 134 of the retainer ring 108. When an internal thread portion 111 provided at the rear end of the fixing member 109 is brought into threadable engagement with the external thread portion 104 of the channel socket 97, the retainer ring 108 is depressed toward the rear end of the channel socket 97 such that the flexible tube 66 is tightly held between the two members, whereby said flexible tube 66 is securely connected to the channel socket 97.

With the channel socket 97 being connected in this way, the front end 114 of the mating portion 105 projects from the front end 134 of the retainer ring 108. The difference between the inside and outside diameters of the mating portion 105 is no more than 0.1 mm at the front end 114. The inner circumference of the portion 105 has a third tapered portion 116 the diameter of which decreases progressively from the front end 114 toward the rear end. The area of the portion 105 which has the smallest diameter provides the smallest channel portion 115, which ensures that when a medical instrument (not shown) of a larger diameter than the channel 70 is inserted, it will stop in that area and will not move any farther to damage the flexible tube 66.

The angle θ formed by the third tapered portion 116 is set at 10 degrees and less to provide maximum protection against the formation of irregularities in the inside diameter. A fourth tapered portion 118 is also provided in that portion of the channel socket 97 which couples the smallest channel portion 115 and the bore 117. The flexible tube 66 fitted over the front end 114 of the mating portion 105 is urged against the first tapered surface 106 by means of a heat shrinking tube 112 such that the flexible tube 66 is connected to the portion 105 with no steps being formed at the joint between the inner surface of the tube 66 and the front end of the mating portion 105.

To prevent buckling of the flexible tube 66, a protective member 113 in the form of a spiral tube such as a densely wound coil spring is slipped over the flexible tube 66 to cover the entire length of the anti-buckle portion 25 stating in the neighborhood of the channel socket 97. The protective member 113 is urged against the flexible tube 66 and fixed thereto by means of the heat shrinking tube 112.

The operational aspect of the first example will now be described. To begin with, the method of assembling the essential part of the endoscope 2 is explained. The flexible tube 66 formed of a comparatively hard resin such as fluororesin is fixed in the insertion section 6, with its length being adjusted to be longer than is actually necessary when the insertion section 6 has been assembled.

The bifurcate tube 67 is soldered not only to the channel socket 97 but also to the suction pipe 98 having the suction socket 99 coupled thereto. Since the coupling method is identical for the two members, discussion will now be made only with respect to the case of coupling the channel socket 97 to the bifurcate tube 67.

The end face of the channel socket 97 which is adjacent to its outer circumferential area that is to be fitted into the hole 101 in the bifurcate tube 67 is covered with a thin layer of solder.

The channel socket 97 is inserted through the hole 101 until it contacts the farthest end and using a soldering iron (not shown), the cutout 102 and end of bifurcate tube 67 are heated to melt the thin film of solder, with the inward projection of the solder being controlled to insure an inside diameter substantially equal to those of the forceps conduit 69 and the bore 117 at the rear end of the channel socket 97 by means of a solder layer control jig (not shown) having substantially the same outside diameter as the inside diameters of the forceps conduit 69 and the bore 117. In this way, solder layer 103 is formed on the inner surface of the channel socket 97 in an area that bridges the forceps conduit 69 and the inner surface of the bore 117 at the rear end of the channel socket 97, whereby the latter is coupled to the flexible tube 66.

To provide strength, solder layer 103 of a sufficient thickness is formed in the cutout 102.

The solder layer 103 formed on the inner surface of the channel socket 97 in the area that bridges the inner surfaces of the forceps conduit 69 and the bore 117 at the rear end of the channel socket 97 to provide a diameter substantially equal to the inside diameters of the bifurcate conduit 69 and the bore 117 at said rear end may be replaced by an adhesive layer. In this alternative case, the channel socket 97 is soldered to the bifurcate tube 67, then an adhesive layer is applied to the inner surface at the joint, the superfluous portion of the applied adhesive is removed with a suitable jig (not shown) such as to control the inward projection of the adhesive, thereby forming a coupling adhesive layer that provides a diameter substantially equal to the inside diameters of the bifurcate conduit 69 and the bore 117 at the rear end of the channel socket 97 and which spans the area bridging the inner surfaces of the forceps conduit 69 and the bore 117.

In the next step, the flexible tube 66 is cut from an end of a cylindrical member 40 to a length that extends to the position where it can be fixed to the channel socket 97. The thus cut tube is inserted into the protective member 113, heat shrinking tube 112, fixing member 109 and retainer ring 108 in that order, with the cut end being the advancing end. Thereafter, the rear end of the flexible tube 66 is thermally processed with a molding jig (not shown) into a shape such as a funnel shape that can be easily inserted into the mating portion 105 of the channel socket 97.

In this thermal processing step, care should be taken to insure that the part of the flexible tube 66 which is to be fitted over the front end 114 of the mating portion 105 will not be subjected to the molding action, thereby assuring that no gap is formed between the flexible tube 66 and the front end 114 of the mating portion 105 when the apparatus is assembled.

As shown in FIG. 3, after the rear end portion of the flexible tube 66 is fitted over the fist tapered surface 106 of the mating portion 105 onto which the adhesive has been extensively applied, the fixing member 109 is brought into threadable engagement with the channel socket 97, whereby the retainer ring 108 is depressed to secure the flexible tube 66 in position. The front end 114 of the mating portion 105 has an outside diameter either equal to or greater than the inside diameter of the flexible tube 66, with the difference being controlled not to exceed 0.6 mm. Thereafter, the protective member 113 is pulled back at a specified position and the heat shrinking tube 112 is placed over a specified area, followed by thermal shrinking so that it is secured to the flexible tube 66.

Then, as shown in FIG. 1, the bifurcate tube 67 is secured to the tubular member 31 by means of screws 68 and the essential part of the manipulating section 3, to which the suction control unit 1, air/water supply nozzle 7, remote switches 8 and angle knobs 9 have been fixed as shown in FIG. 2, is secured by means of fixing frame 33, shims 34a and 34b and screws 35.

Subsequently, the grip 30 is inserted from the distal end of the insertion section 6 and fixed in position by threadable engagement with the grip fixing ring 37. In this case, the tubular member 31 is withdrawn by a length of about 0.5 mm due to an external force such as the elastic deformation of the fixing frame 33 and the position of the mounting hole 77 in the grip 30 is allow for this displacement.

Then, as shown in FIG. 1, the connection cylinder 78 having the O-ring 81 fitted therein is inserted into the mounting hole 77 and the thread portion 79 is brought into threadable engagement with the thread portion 76 of the bifurcate tube 67, whereby the connection cylinder 78 is secured relative to the bifurcate tube 67. The connection cylinder 78 has the circular hole 80 formed therein and the packing 83 is fixed to the end face 84 of the circular hole 80 by means of a silicone-base adhesive and, in addition, the forceps socket 82 having the O-rings 93 and 94 fitted therein is inserted into the circular hole 80 and positioned such that the forceps socket 82 is prevented from rotating by means of anti-rotation members 75 and chamfered portions 91.

Subsequently, the retainer tube 87 is brought into threadable engagement with the thread portion 86 of the connection cylinder 78 and the flange 88 on the forceps socket 82 is depressed so that the latter is urged against the end face 85 of the bifurcate tube 67 and fixed in position. Thus, the packing 83, the forceps conduit 69 and the conduit 90 have substantially the same inside diameter and the two conduits are connected together without any step formed at the joint. The allowance by which the packing 83 is to be compressed is controlled by its length along the conduit 90 and the depth of the circular hole 89.

After the packing 83, the forceps conduit 69 and the conduit 90 have been connected, the cover member 95 is fitted into the mounting hole 77, whereby it is fixed flush with the projection 61 from the grip 30.

In the next step, the anti-buckle portion 25 comprising a cover 51 and a socket 49 is fitted over the connecting member 42 from the distal end of the insertion section 6. As shown in FIG. 1, the cover 51 has a groove 58 to which a flange 52 on the socket 49 is bonded. The thread portion 50 of the anti-buckle portion 25 is brought into threadable engagement with the tubular member 31 until it contacts the grip fixing rig 37 and fixed in position. Just before this step, the cylindrical member 40 having the O-ring 54 fitted therein is placed in order to insure watertightness for both the grip 30 and the tubular member 31.

Then, the inner surface of the distal end of the cover 51 is bonded and fixed to a jacket tube 46 on the insertion section 6. In the assembling operation described above, the endoscope 2 may use different diameters of the insertion section 6 but the grip fixing ring 37, connecting member 42 and O-ring 53 are common and this contributes to the use of a smaller number of parts. The O-ring 53 insures high degree of watertightness for varying diameters of the insertion section 6.

The first example of the invention offers the following advantages. As shown in FIG. 3, the endoscope 2 according to the first example has the flexible tube 66 connected to the channel socket 97 on the bifurcate tube 67 in such a way that the front end 114 of the channel socket 97 projects toward the distal end beyond the front end 134 of the retainer ring 108 and the heat shrinking tube 112 is shrunk-fitted over the flexible tube 66 which has been slipped over the projecting mating portion 105, whereby the flexible tube 66 is firmly depressed onto the thick-walled part of the first tapered portion 106 of the channel socket 97 which is distant from the front end 114; thus, high rigidity is insured and yet no filth-collecting gaps are formed on the inner circumference of the joint between the flexible tube 66 and the channel socket 97 and this contributes to greater ease in the cleaning operation.

The heat shrinking tube 112 also serves to prevent the flexible tube 66 from buckling; even if a bending force is exerted on the flexible tube 66, the heat shrinking tube 112 prevents it from buckling at the front end 114 of the channel socket 97 and it also ensures against the creation of filth-collecting gaps at the joint between the flexible tube 66 and the channel socket 97.

The outside diameter of the front end 114 of the channel socket 97 is either equal to or greater than the outside diameter of the flexible tube 66, with the difference not exceeding 0.6 mm; this dimensional relationship insures that the flexible tube 66 is depressed with greater force to the channel socket 97 at its front end 114.

The difference between the inside and outside diameters of the channel socket 97 at the front end 114 is no more than 0.1 mm and it can be fixed to create very few steps on the inner surface. Hence, the channel socket 97 can be joined to the flexible tube 66 without creating any filth-collecting gaps on the inner circumference and the interior of the joint can be cleaned with improved efficiency since the cleaning brush will contact the interior evenly to shorten the time of cleaning under running water.

The third tapered portion 116 which is formed to provide an angle of no more than 10 degrees on the inner circumference of the front end 114 of the channel socket 97 ensures the smallest channel diameter and yet reduces the size of steps that may be formed at the joint between the channel socket 97 and the flexible tube 66.

The first tapered portion 106 of the channel socket 97 is bonded to the inner surface of the flexible tube 66 and this insures that no filth-collecting gaps will be formed on the inner circumference of the joint between the two members.

As shown in FIG. 1, the connection cylinder 78 is inserted into the mounting hole 77 in the grip 30 and fixed to the bifurcate tube 67 so as to provide the circular hole 80; thereafter, the forceps socket 82 is inserted into the circular hole 80 and depressed against the bifurcate tube 67 and fixed in position such that connection to the conduit is established without forming any steps at the joint and this allows the forceps socket 82 to be joined to the bifurcate tube 67 without creating any filth-collecting gaps on the inner circumference of the joint. Hence, the interior of the joint can be cleaned with improved efficiency since the cleaning brush will contact the interior evenly to shorten the time of cleaning under running water. In addition, the resin-molded grip 30 has no thread portions and can hence maintain high strength.

The forceps socket 82 has two chamfered portions on the outer circumference of the area near the lower end and they are to be fitted between two anti-rotation members 75; this prevents the forceps socket 82 from rotating relative to the bifurcate tube 67, thereby enabling the provision of an anti-rotation mechanism having great strength.

The packing 83 is bonded to the end face 84 of the forceps socket 82 with a silicone-base adhesive and this ensures against dislodging of the packing 83 during the step of connecting the forceps socket 82 to the bifurcate tube 67.

At the solder-connected joint of conduits, the depth by which the channel socket 97 is inserted into the bifurcate tube 67 is adjusted to be substantially equal to the depth of the cutout 102 and this allows a thick solder layer 103 to be formed in the cutout 102 thereby increasing the strength of the joint. In addition, the area over which the soldering iron is applied is sufficiently increased to provide a greater chance for the molten solder layer 103 to flow into areas other than the cutout 102.

The solder or adhesive layer which is substantially equal to the inside diameters of the channel socket 97 and the bifurcate tube 67 is formed on the inner circumference of the joint in the area that spans the two members; this ensures that they can be joined together without creating any filth-collecting gaps on the inner circumference of the joint and its interior can be cleaned with improved efficiency since the cleaning brush will contact the interior evenly to shorten the time of cleaning under running water.

We next describe the second example of the invention.

Figure 4:
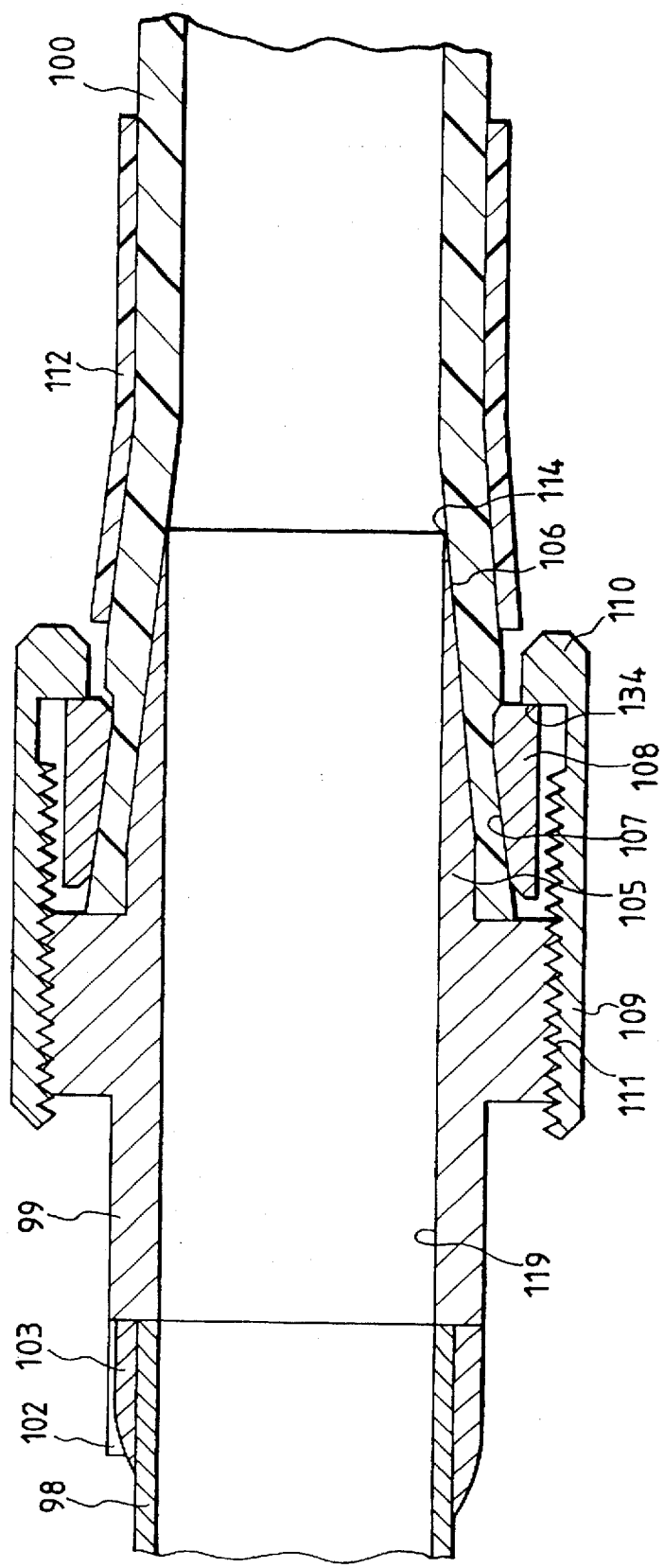
FIG. 4 is an enlarged section of the joint at which the suction socket connected to the suction pipe is coupled to the suction tube in an endoscope according to a second embodiment of the invention.

FIG. 4 is an enlarged section of the joint at which the suction socket 99 connected to the suction pipe 98 as shown in FIG. 1 is coupled to the suction tube 100.

As already mentioned in connection with the first example, the suction pipe 98 is soldered to the suction socket 99. The bore 119 of the suction socket 99 is substantially equal in inside diameter to the suction pipe 98 over the entire length; the outside diameter of the front end 114 of the suction socket 99 is either equal to or greater than the inside diameter of the suction tube 100, with the difference being no more than 0.6 mm as in the first example.

The flexible tube 66 and the channel socket 97 are connected in the same manner as in the first example and the description of the resulting joint is omitted. The description of other aspects of the second example that are identical to the first example in terms of construction and the mechanism of action is replaced with the identification of relevant parts and components by like numerals. The following description is hence directed to only those aspects which differ from the first example.

The method of constructing the joint of the flexible tube 66 to the channel socket 97 is also substantially the same as in the first example, except that the protective member 113 is not used; hence, the description of the method is also omitted.

The third tapered portion 116 provided in the first example is absent from the second example and no steps are created on the inner circumference of the joint between the flexible tube 66 and the channel socket 97, which contributes to even better efficiency in the cleaning operation.

Figure 5A:
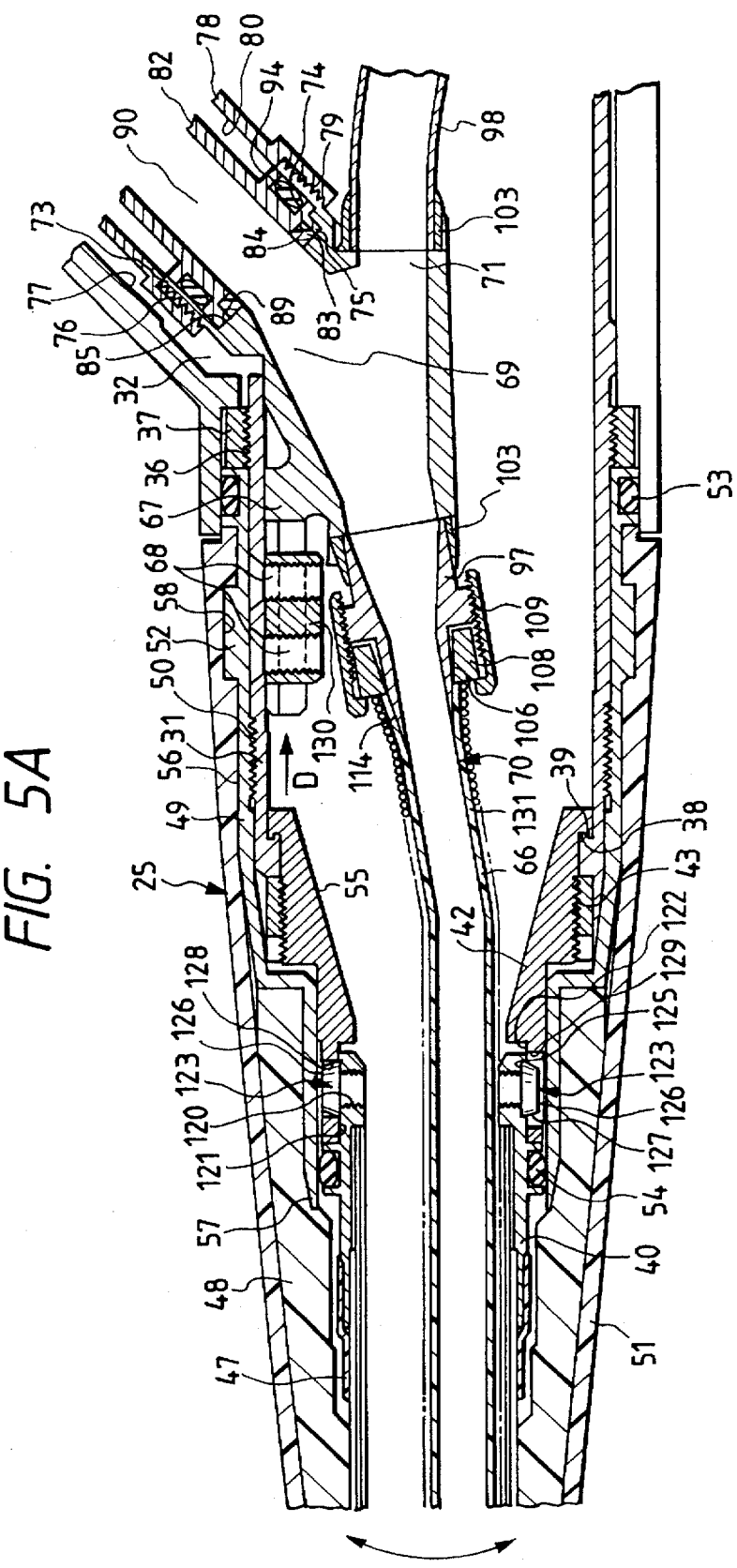
FIG. 5A is a sectional view showing the area around the joint between the manipulating and insertion sections of an endoscope according to a third embodiment of the invention.
Figure 5B:
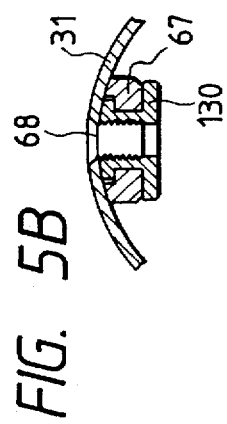
FIG. 5B is a side view of the joint between the bifurcate tube and the tubular member in the endoscope as seen in the direction of arrow D.
Figure 6:
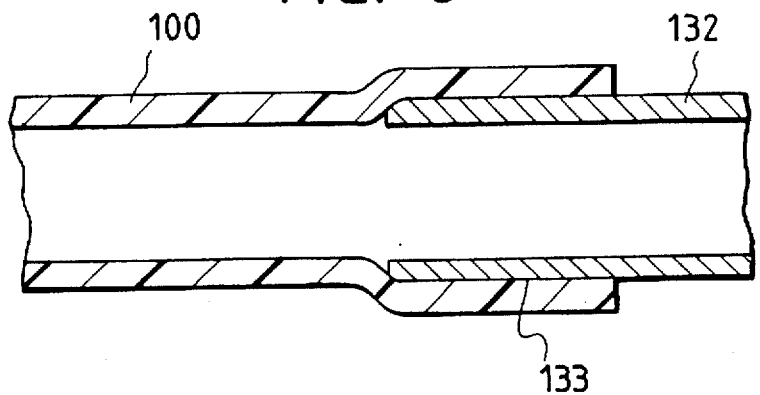
FIG. 6 is a sectional view showing the joint between the suction tube and the pipe connected to the suction control unit in the endoscope.

The third example of the invention will now be described with reference to FIGS. 5 and 6. FIGS. 5A is a sectional view showing the area around the joint between the manipulating section 3 and the insertion section 6; FIG. 5B is a side view of the joint between the bifurcate tube 67 and the tubular member 31 as seen in the direction of arrow D; and FIG. 6 is a sectional view showing the joint between the suction tube 100 and a pipe 132 connected to the suction control unit 1.

The connecting member 42 which is provided with a cutout 42a of width t along the entire length as in the first example is fixed to the tubular member 31. The cylindrical member 40 is also fixed to the outer jacket of the insertion section 6 as in the first example. The description of other aspects of the third example that are identical to the first example in terms of construction and the mechanisms of action is replaced with the identification of relevant parts and components by like numerals. The following description is hence directed to only those aspects which are different from the first example.

As shown in FIG. 5A, the cylindrical member 40 has at least two internal threads 120 on the outer circumference 121, the portion of which is inserted into the bore 122 of the connecting member 42 and screws 123 are threaded into the respective internal threads 120 so as to fix the cylindrical member 40. A radial clearance is provided between the outer circumference 121 and the bore 122 such that the total clearance across the bore is about 0.2 mm.

The head 124 of each screw 123 has a taper 127 the diameter of which increases progressively from its top 126 to the bottom 125. While at least two screws 123 are provided, one of them has its head inserted into one small-diameter hole 128 provided in the connecting member 42 and the other screws 123 have their head 124 inserted into large-diameter holes provided in the corresponding positions.

The small-diameter hole 128 is of such a size that the bottom 125 of the head 124 of the screw 123 can be snugly fitted into this hole. The large-diameter hole 129 has a fairly grater diameter than the bottom 129.

Since the screw 123 has its head 124 inserted into the small-diameter hole 128, the cylindrical member 40 and the connecting member 42 are joined with their positions being practically fixed in both the longitudinal and radial directions of the insertion section 6.

As shown in FIGS. 5A and 5B, the bifurcate tube 67 is longitudinally slidable as it is held between the tubular member 31 and a guide 130 fixed thereto by means of screws 68.

The joint at which the flexible tube 66 is fixed to the channel socket 97 has essentially the same structure as in the first example except on the following points: a spiral tube having a smaller inside diameter than the outside diameter of the flexible tube 66 serves as the protective member 113 used in the first example and it is slipped over and pressed against the flexible tube 66 which has been slipped over the front end 114 of the channel socket 97.

As shown in FIG. 6, the suction tube 100 has its conduit communicate with the pipe 132 connected to the suction control unit 1 in the manipulating section 3 and this is accomplished by applying an adhesive to the mating portion 133 and the mating end of the pipe 132 and then fixing the two members together; because of this design, no filth-collecting gaps are formed in the interior of the joint.

The method of assembling the construction of the third example is essentially the same as in the first example and the following description is directed to only those aspects which differ from the first example.

The method starts with fixing the flexible tube 66 to the channel socket 97 in the same manner as in the first example. Then, the spiral tube 131 is slipped over and fixed to the flexible tube 66 which has been slipped over the front end 144 of the channel socket 97.

As in the first example, the necessary parts or components are inserted into the connecting member 42, which is then slipped over the cylindrical member 40 and fixed to the latter by means of screws 123 which are threaded into small-diameter hole 128 and large-diameter hole 129; the connecting member 42 is thus joined to the cylindrical member 40 and, as in the first example, the tubular member 31 is fixed to the connecting member 42.

In the next step, the guide 130 is set on the bifurcate tube 67 and fixed to the tubular member 31 by means of screws 68 such that the bifurcate tube 67 is held to be longitudinally slidable between the tubular member 31 and the guide 130.

The subsequent steps are essentially the same as in the first example and need not be described. We then describe the mechanism of action that is peculiar to the third example.

The connecting member 42 is joined to the cylindrical member 40 by means of the screw 123 which has its head 124 inserted into the small-diameter hole 128. Because of the clearance that exists between the bore 122 of the connecting member 42 and the outer circumference 121 of the cylindrical member 40, the latter is capable of pivoting on the head 124 of screw 123 to move back and forth in the plane of FIG. 5A and the angle through which it can pivot is limited by the contact the outer circumference 121 makes with the bore 122.

The cylindrical member 40 is also capable of pivoting on the head 124 of screw 123 in a direction normal to the plane of FIG. 5A and the angle through which it can pivot is again limited by the contact the outer circumference 121 makes with the bore 122. In this way, the insertion portion 6 is adapted to be pivotal relative to the manipulating portion 3.

As already mentioned, the bifurcate tube 67 is held between the tubular member 31 and the guide 130 such that it is longitudinally slidable. When the connection cylinder 78 is inserted into the mounting hole 77 such that it is fixed to the bifurcate tube 67, it is necessary that the latter be adjusted by suitable means such as tweezers (not shown)

that are inserted into the circular hole 80 in the connection cylinder 78 such that the thread portion 76 of the bifurcate tube 67 will be positioned coaxially with the mounting hole 77.

The thus assembled endoscope 2 of the third example not only retains the advantages of the first example of the invention but also presents its own advantages. First, in order to join the flexible tube 66 to the channel socket 97 on the bifurcate tube 67, the spiral tube 131 serving as the protective member 113 which has been slipped over the entire length of the anti-buckle portion 25 is slipped as such to be placed over the flexible tube 66 after the latter has been slipped over the front end 114 of the channel socket 97 and the spiral tube 131 is then urged to be fixed to the tube 66. Because of this arrangement, the flexible tube 66 is firmly depressed onto the first tapered portion 106 of the channel socket 97, thereby insuring that no filth-collecting gaps will be created on the inner circumference of the joint between the flexible tube 66 and the channel socket 97; in addition, the number of the parts that have to be assembled is sufficiently reduced to provide operational ease.

Secondly, the cylindrical member 40 at the end of the insertion section 6 is joined to the manipulating section 3 by means of the connecting member 42, which is connected to the cylindrical member 40 in such a way that the latter is capable of pivoting in the presence of the clearance between those two members and this ensures the insertion section 6 to be pivotal relative to the manipulating section 3.

This offers the advantage that even if the insertion section 6 is inserted into a cavity in the patient's body to such a depth that the length of insertion almost reaches the anti-buckle portion 25, the area near that portion 25 can be bent by exerting a force on the insertion section without causing any discomfort to the patient.

Thirdly, the connecting member 42 is jointed to the cylindrical member 40 by means of at least two screws 123 which have their heads 124 fitted into the small-diameter hole 128 and large-diameter hole 129 in the outer circumference of the connecting member 42 such that those screws are brought into threadable engagement with the holes and by then fitting the anti-buckle socket 49 over the connecting member 42. This arrangement insures that even if the screws 123 loosen, they will not slip out completely and there is no possibility that the connecting member 42 will separate from the cylindrical member 40, which would otherwise cause the destruction of the parts or components incorporated within the conduit.

Fourthly, the screw 123 is inserted into the small-diameter hole 128 by having the bottom 125 of its head 124 snugly fitted into the hole and hence the cylindrical member 40 and the connecting member 42 are joined together in such a way that their positions are practically fixed in both the longitudinal and radial directions of the insertion section 6.

Fifthly, the bifurcate tube 67 is adapted to be slidable longitudinally so that, when assembling the endoscope 2, the connection cylinder 78 can be mounted n such a way that the mounting hole 77 in the grip 30 is completely coaxial with the forceps conduit 69 in the bifurcate tube 67. This arrangement ensures that even if the number of parts to be assembled increases to cause greater dimensional variations, no extra force will be exerted on a limited area of the grip 30 and, in addition, the desired water-tightness is assured in a consistent manner.

We now describe the fourth example of the invention.

Figure 7:
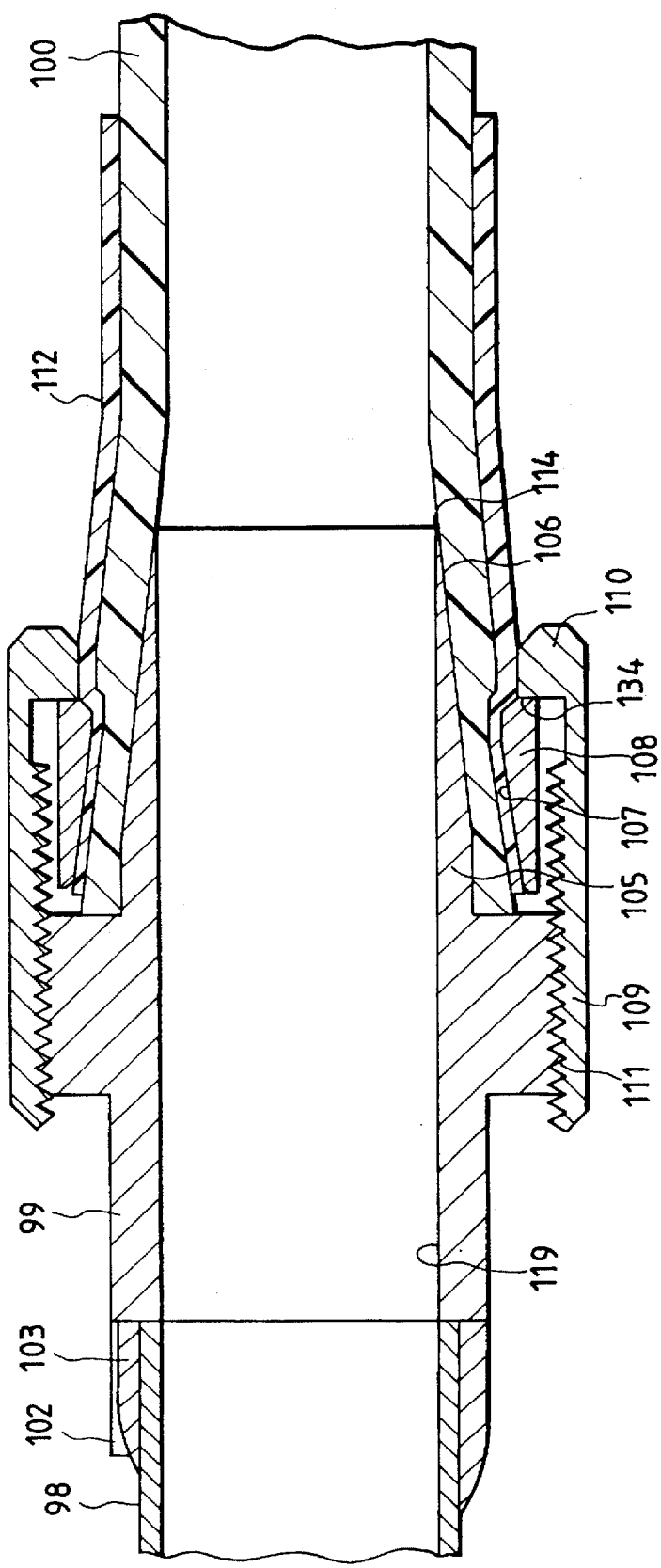
FIG. 7 is an enlarged section showing how the suction socket 99 connected to the suction pipe 98 is joined to the suction tube in an endoscope according to a fourth embodiment of the invention.

FIG. 7 is an enlarged section showing how the suction socket 99 connected to the suction pipe 98 is joined to the suction tube 100 by a different method than in the second example. The description of other aspects of the fourth example which are identical to the second example in terms of construction and the mechanism of action is replaced with the identification of relevant parts and components by like numerals and the following description is directed to only those aspects which are different from the second example.

The suction tube 100 is fitted over the first tapered surface 106 of the mating portion 105 of the suction socket 99 and bonded to the latter. The heat shrinking tube 112 is then shrunk-fitted over and fixed to the outer circumference of the suction tube 100. The second tapered portion 107 of the retainer ring 108 is pressed onto the outer circumference of the tube 112 by means of the fixing member 109, whereby the suction tube 100 is connected and fixed to the suction socket 99.

The method of constructing the connection device of the fourth example is essentially the same as in the first example. It starts with inserting the suction tube 100 over the first tapered surface 106 of the mating portion 105 of the suction socket 99. Then, the heat shrinking tube 112 is heated to shrink on the suction tube 100 which has been snugly fitted over substantially all part of the first tapered surface 106. After the heat shrinking tube 112 has been fixed in position, the retainer ring 108 is pressed onto the outer circumference of the tube 112 by means of the fixing member 109 so that the suction tube 100 is connected to the suction socket 99.

The other aspects of the method of interest are identical to those of the second example and need not be described here.

The fourth example described above not only retains the advantages of the second example but also affords its own advantage of insuring that the heat shrinking tube can be fixed more firmly to the outer circumference of the suction tube 100.

Figure 8:
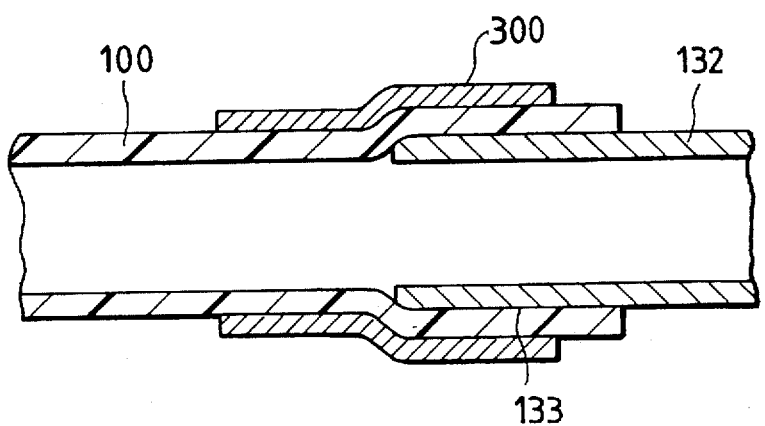
FIG. 8 is a longitudinal sectional view showing the joint between the pipe and the flexible tube according to a fifth embodiment of the invention.

FIG. 8 is a longitudinal sectional view showing the joint between the pipe and the flexible tube according to a fifth embodiment of the invention. As shown in FIG. 8, the outer surface of the suction tube 100 at the junction of the suction tube 100 and the pipe 132 is covered directly with a heat shrinking tube 300 so that the suction tube 100 is forcedly depressed onto the pipe 132. One end of the heat shrinking tube 300 extends over a distal end of the pipe 132 toward the bifurcate tube 67 whereas the other end of which extends thereover toward the suction control unit 1. The design of this embodiment is advantageous in that no filth-collecting gaps are formed in the interior of the joint.

Figure 9:
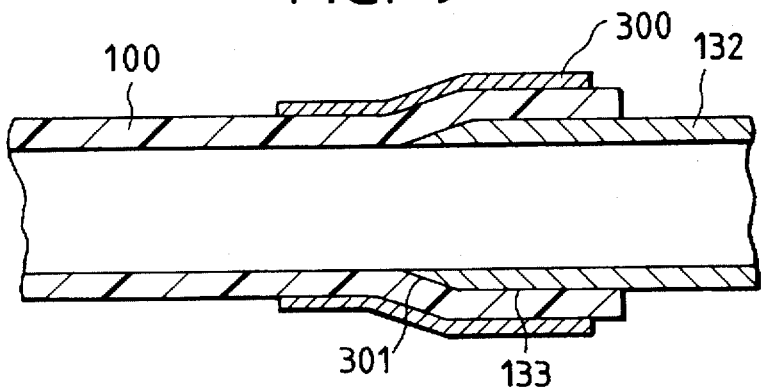
FIG. 9 is a longitudinal sectional view showing an arrangement of the joint between the pipe and the flexible tube shown in FIG. 8.

FIG. 9 is a longitudinal sectional view showing an arrangement of the joint between the pipe and the flexible tube shown in FIG. 8. As shown in FIG. 9, a distal end of a mating portion 133 of the pipe 132 is formed with a tapered portion 301 the diameter of which decreases progressively toward the distal end of the pipe 132. An adhesive may be applied to the mating portion 133 to firmly secure it to the suction tube 100 to connect the conduits to each other, so that furthermore no filth-collecting gaps are formed in the interior of the joint between the suction tube 100 and the pipe 132. In this regard, when the adhesive is applied to the tapered portion 301 of the mating portion 133, the adhesive should be applied from distance of 0.5 mm from the distal end of the pipe 132 to avoid swelling the adhesive out of the joint. Further, similar to the fifth embodiment shown in FIG. 8, the outer surface of the suction tube 100 at the junction of the suction tube 100 and the pipe 132 is covered directly with a heat shrinking tube 300 so that the suction tube 100 is forcedly depressed onto the pipe 132. One end of the heat shrinking tube 300 extends over a distal end of the pipe 132 toward the bifurcate tube 67 whereas the other end of which extends over the distal end of the pipe 132 and over the tapered portion 301 toward the suction control unit 1.

Figure 10:
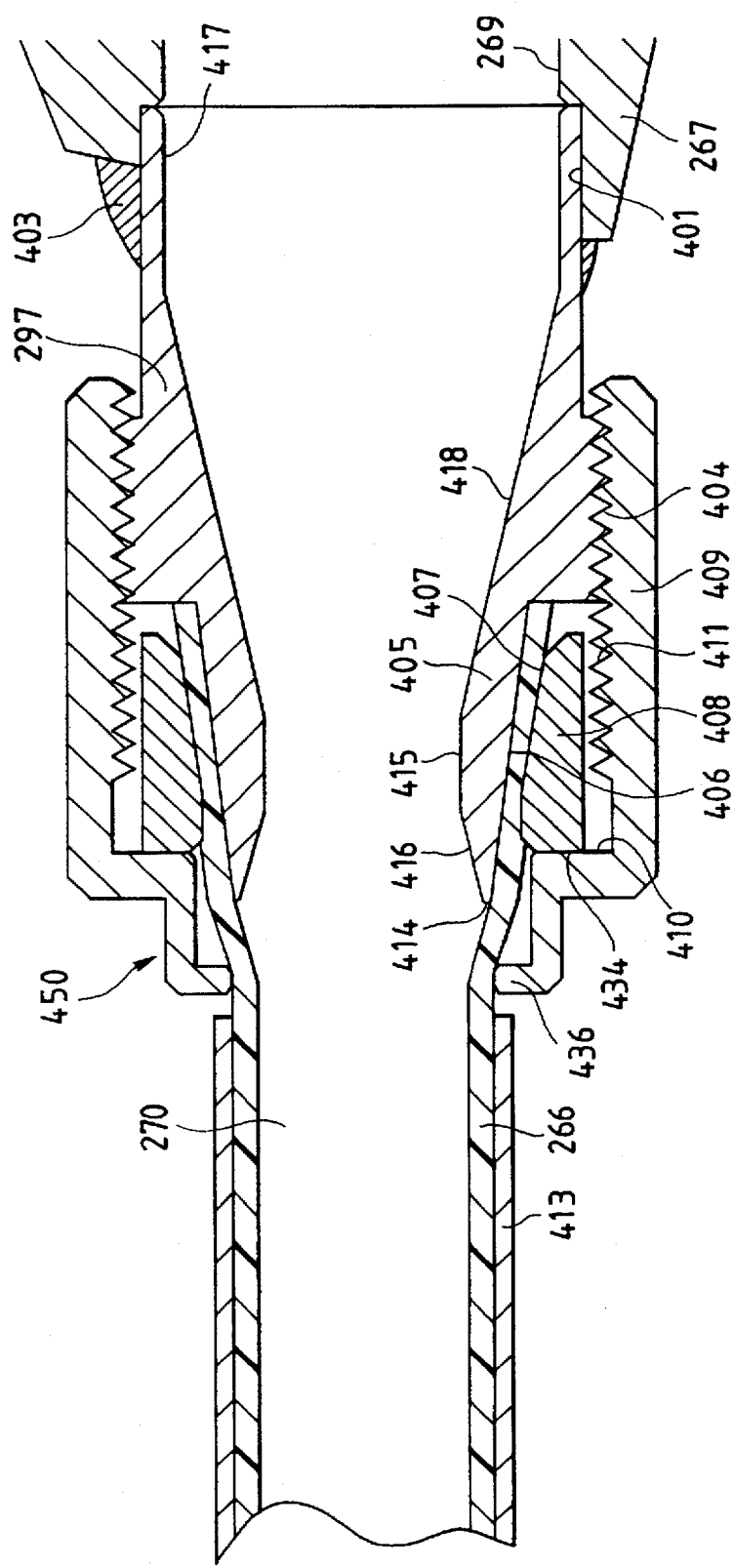
FIG. 10 is a longitudinal cross-sectional view of a joint jointing together a bifurcated tube body and a flexible tube of an endoscope according to a sixth embodiment of the present invention.

FIG. 10 is a longitudinal cross-sectional view of a joint jointing together a bifurcated tube body and a flexible tube of an endoscope according to a sixth embodiment of the present invention.

As shown in FIG. 10, a channel socket 297 for connecting a flexible tube 266 to a bifurcated tube body 267 includes an external thread 404 having a large diameter and a mating section 405 having a smaller diameter. The rear end of the flexible tube 266 is fitted over the mating section 405. A first tapered section 406 is formed on the outer peripheral surface of the mating section 405 such that the diameter of the first tapered section becomes larger from a front end 414, i.e., an open end, to the rear end of the insertion section. The rear portion of the mating section 405 has a larger thickness compared with the front end thereof.

The rear end of the flexible tube 266 is fitted over the first tapered section 406. A ring-shaped retainer 408 is fitted over the outer peripheral surface of the area of the flexible tube 266 which covers the first tapered section 406. The ring-shaped retainer 408 has a second tapered section 407 which has a larger diameter from an abutment surface 434 formed at the front end toward the rear end of the retainer 408.

The abutment surface 434 of the retainer 408 abuts against a stepped abutment surface 410 formed along the inner peripheral surface of the front end of a clamping member 409. As a result of the external thread 404 of the channel socket 297 being screwed into an internal thread section 411 formed along the inner peripheral surface of the rear end of the clamping member 409, the retainer 408 is pushed toward the rear end of the channel socket 297. As a consequence of this pushing action, the flexible tube 266 fitted over the outer peripheral surface of the mating section 405 is fixedly held, and the end of the flexible tube 266 is fixed around a rear thick portion of the channel socket 297 with respect to the front end 414.

The front end 414 of the mating section 405 of the channel socket 297 is formed to have a diameter which is equal to or larger than the inside diameter of the flexible tube 266. The mating section 405 also has a third tapered section 406 which has a gradually smaller inside diameter toward the rear end of the insertion section. The area of the third tapered section 406 that has the smallest inside diameter forms a smallest channel section 415 which has the smallest inside diameter in a channel 270. If a medical instrument (not shown) whose diameter is larger than the inside diameter of the channel 270 is inserted into the channel, the medical instrument will be stopped here to prevent damage on the flexible tube 266 provided in a forward position with respect to the smallest channel section.

The smallest channel section 415 and a bore 417 formed in the rear end of channel socket 297 are connected together by a fourth tapered section 418. This fourth tapered section 418 has a larger diameter toward the rear end of the channel socket.

In the sixth embodiment, a flange 436 is formed on the front end of the clamping member 409 so as to have a diameter which is smaller than the outside diameter of the leading end 414 of the channel socket 297. The flange 436 presses an area located slightly forward with respect to the portion of the flexible tube 266 which is fixed to the mating section 405 of the channel socket 297, in a radially inward direction. The flexible tube 266 is therefore prevented from moving in a radially outward direction. If the flange does not press the flexible tube, the flexible tube 266 will inflate outwards with respect to the outer peripheral surface of the mating section 105. As a result of at least the flexible tube 266 moving away from the outer peripheral surface of the front end 414, a gap is formed between the front end 414 of the channel socket 297 and the internal peripheral surface of the flexible tube 266 which outwardly moved away from the front end 414. The flange 36 constitutes regulating means for preventing the formation of the gap.

Specifically, as a result of the external thread 404 being screwed into the internal thread 411 of the channel socket 297, the retainer 408 pressingly fixes the rear end of the flexible tube 266 around the outer periphery of the mating section 405. Concurrently, the flange 436 formed at the front end of the clamping member 409 presses the portion of the flexible tube 266 extending forward from the front end 414, in a radially inward direction. As a result, the flexible tube 266 extends to have a smaller diameter as it is tapered from the front end 414, as shown in FIG. 10. The internal peripheral surface of the flexible tube 266 smoothly extends in a forward direction from the front end 414 of the channel socket 297 without forming the above described gap. The flexible tube is regulated such that the internal peripheral surface of the portion of the flexible tube 266 outside the front end 414 comes into close contact with the outer peripheral surface of the front end 414 along the entire circumference thereof, thereby preventing the creation of the gap which would otherwise collect dirt and the like.

The internal peripheral surface of the flexible tube 266, which is tapered forwardly from the front end 414 of the channel socket 297, has a larger diameter in the direction opposite to the third tapered section 416. In other words, the flexible tube has a larger diameter toward the rearward direction thereof. With this construction, if dirt sticks to the internal peripheral surface of the tapered section, the dirt can be easily and quickly removed by pouring, e.g., a cleansing fluid, into the tube, because the cleansing fluid extends into every part of the tube along the smoothly connected surface between the flexible tube 266 and the channel socket 297.

To prevent the buckling of the flexible tube 266, the flexible tube 266 is fixedly sheathed with a protecting tube 413, such as a heat shrinkable tube, so as to cover a length of about 8 mm from the portion of the flexible tube in vicinity of the channel socket 297.

The method of putting together the flexible tube 266 and the channel socket 297 will now be described.

When an insert is assembled, the flexible tube 266 made from relatively hard resins such as fluororesins is fixed into the insert in such a length as to be longer than the length actually required after the assembly of the insert. The bifurcated tube body 267 is connected to a suction pipe with solder in the same manner as the channel socket 297. Since the connection between the bifurcated tube body and the suction pipe is the same as the connection between the bifurcated tube body and the channel socket, only the latter connection will be described.

A thin layer of solder is previously applied on the outer periphery of the end of the channel socket 297 which is to be fitted into a hole 401 of the bifurcated tube 267. The end of the channel socket 297 is inserted into the hole 401 until it comes into abutment against the bottom of the hole 401. The thinly pre-coated solder layer is fused with a soldering iron (not shown) so as to prevent the solder from flowing into the internal peripheral surface of a forceps conduit 269 and the bore 417 of the channel socket 297 by controlling the time required to heat a cutout and the end of the bifurcated tube body 267. Thus, the bifurcated tube body 267 and the channel socket 297 are joined together.

At this time, a thick solder layer 403 is formed to afford strength to the cutout. The flexible tube 266 is cut to such a length that it can be fixed to the channel socket 297. Subsequently, the cut end of the flexible tube 266 is guided to pass through the protecting member 413, the clamping member 409, and the retainer 408, in that order. The end of the flexible tube 266 is molded into a shape which facilitates the insertion of the mating section 405 of the channel socket 297 into the tube using a molding jig (not shown); namely, the end of the flexible tube is flared so as to have a larger diameter upon heat.

In the molding process, the portion of the flexible tube 266 which is to be fitted over the front end 414 of the mating section 405 is prevented from being flared, thereby ensuring the prevention of creation of a gap between the flexible tube 266 and the front end 414 of the mating section 405 when the flexible tube and the channel socket are assembled into a unit.

After the flexible tube 266 has been fitted over the first tapered section 406 of the mating section 405, the retainer 408 is pressed to secure the flexible tube in position as a result of the clamping member 409 being engaged with the channel socket 297. In this event, the external peripheral surface of the flexible tube 266 is pressed by the inner periphery of the flange 436 of the clamping member 409 such that the diameter of the flexible tube becomes smaller. The flexible tube 266 is resultantly pressed toward the front end 414, so that it is prevented from moving in a radially outward direction. The front end 414 of the mating section 405 is brought into close contact with the internal peripheral surface of the portion of the flexible tube 266 which covers the front end, which prevents the creation of gaps which would otherwise collect dirt. The protecting member 413 is withdrawn to a predetermined location and is subjected to a heat shrinking operation, whereby the flexible tube 266 is fixedly sheathed with the protecting member.

In the joint assembly consisting of the flexible tube 266 and the channel socket 297 of the bifurcated tube body 267, the external thread 404 of the channel socket 297 is screwed into the internal thread 411 of the clamping member 409. As a result, the second tapered section 407 of the retainer 408 presses the outer periphery of the rear end of the flexible tube 266 covering the first tapered section 406 of the channel bracket 297, so that the flexible tube is secured. At the same time, the flange 436 of the clamping member 409 inwardly presses the portion of the flexible tube 266 in the vicinity of the front end 414, whereby the flexible tube 266 is pressed against the thick portion of the mating section distant from the front end 414 of the first tapered section 406 of the channel socket 297. As a result, it becomes possible to fixedly connect the flexible tube 266 to the channel socket 297 while the high rigidity of the flexible tube is ensured. Further, if the medical instrument, and the like, exerts a force on the internal peripheral surface of the flexible tube 266 via the front end 414 of the channel socket 297, the internal peripheral surface of the flexible tube 266 can be held in close contact with front end 414. No gaps which would otherwise collect dirt are created between the internal peripheral surface of the flexible tube and the front end of the channel socket. For this reason, the joint between the flexible tube and the channel socket can be easily cleansed in a short period of time, and therefore superior cleansing property of the joint can be maintained.

The protecting member 413 also prevents the buckling of the flexible tube 266. Therefore, if a bending force acts on the flexible tube 266, it is possible to prevent the portion of the flexible tube 266 located in the vicinity of the front end 414 of the channel socket 297 from buckling up.

Figure 11:
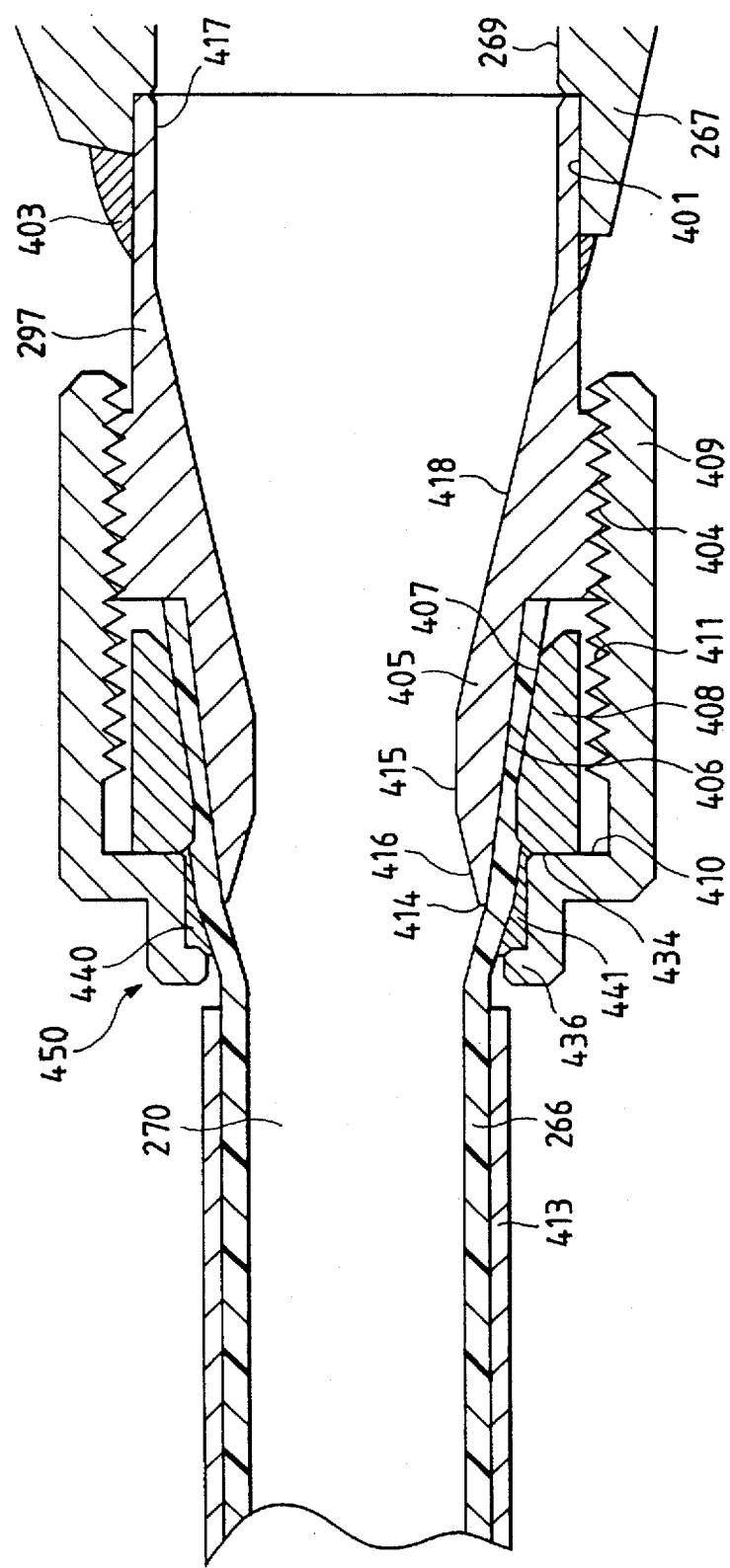
FIG. 11 shows the construction of the neighborhood of a tube connector according to a seventh embodiment of the present invention.

FIG. 11 shows the construction of the neighborhood of a tube connector 450 according to a seventh embodiment of the present invention. The seventh embodiment is the same as the sixth embodiment only except for a difference with regard to the inside diameter of the flange 436 of the clamping member 409. The inside diameter of the flange 436 is larger than the outside diameter of the flexible tube 266 fitted over the front end 414 of the channel socket 297, and hence the flange 436 does not press the flexible tube 266. However, a space 441 formed between the flange 436, the outside diameter of the flexible tube 266, and the abutment surface 434 of the retainer 408 is filled with an adhesive 440.

The adhesive 440 prevents the portion of the flexible tube 226 fitted over the front end 414 of the channel socket 297 from moving in a radially outside direction. The internal circumference of the flexible tube 266 outside the front end 414 is prevented from being spaced away from the outer periphery of the front end 414; namely, the internal circumference of the flexible tube remains in close contact with the external periphery of the front end 414. Since the connector of the seventh embodiment is identical with that of the sixth embodiment in other respects, their explanation will be omitted here.

The method of putting together the flexible tube 266 and the channel socket 297 will now be described.

As with the sixth embodiment, the flexible tube 266 is cut to such a length that it can be fixed to the channel socket 297. Subsequently, the cut end of the flexible tube 266 is guided to pass through the protecting member 413, the clamping member 409, and the retainer 408, in that order. The end of the flexible tube 266 is molded into a shape which facilitates the insertion of the mating section 405 of the channel socket 297 into the tube using a molding jig (not shown); namely, the end of the flexible tube is flared upon heat.

In the molding process, the portion of the flexible tube 266 which is to be fitted over the front end 414 of the mating section 405 is prevented from being flared, thereby ensuring the prevention of creation of a gap between the flexible tube 266 and the front end 414 of the mating section 405 when the flexible tube and the channel socket are assembled into a unit. After the flexible tube 266 has been fitted over the first tapered section 406 of the mating section 405, the retainer 408 is pressed to secure the flexible tube in position as a result of the clamping member 409 being engaged with the channel socket 297.

In this event, the external peripheral surface of the flexible tube 266 is not pressed by the inner periphery of the flange 436 of the clamping member 409. The space 441 formed in the vicinity of the flange 436, the outer periphery of the flexible tube 266, and the abutment surface 434 of the retainer 408 is filled with the adhesive 440. As a result, the portion of the flexible tube 226 positioned in the neighborhood of the front end 414 is prevented from moving, which in turn prevents the creation of a gap which would otherwise collect dirt between the flexible tube 266 and the front end 414. Next, the protecting member 413 is withdrawn to a predetermined location and is subjected to a heat shrinking operation, whereby the flexible tube 266 is fixedly sheathed with the protecting member.

In the joint assembly consisting of the flexible tube 266 and the channel socket 297 of the bifurcated tube body 267, the external thread 404 of the channel socket 297 is screwed into the internal thread 411 of the clamping member 409. As a result, the second tapered section 407 of the retainer 408 presses the outer periphery of the rear end of the flexible tube 266 fitted over the first tapered section 406 of the channel bracket 297, so that the flexible tube is secured. At the same time, as a result of the space 441 being filled with the adhesive 440, the flexible tube 226 is firmly pressed against the thick portion of the mating section away from the front end 414 of the first tapered section 406 of the channel socket 297, thereby the high rigidity of the flexible tube being ensured. Further, if the medical instrument, and the like, exerts a force on the flexible tube 266, no gaps which would otherwise collect dirt will be created between the flexible tube 266 and the front end 414. For this reason, the superior cleansing property of the joint is attained.

Figure 12:
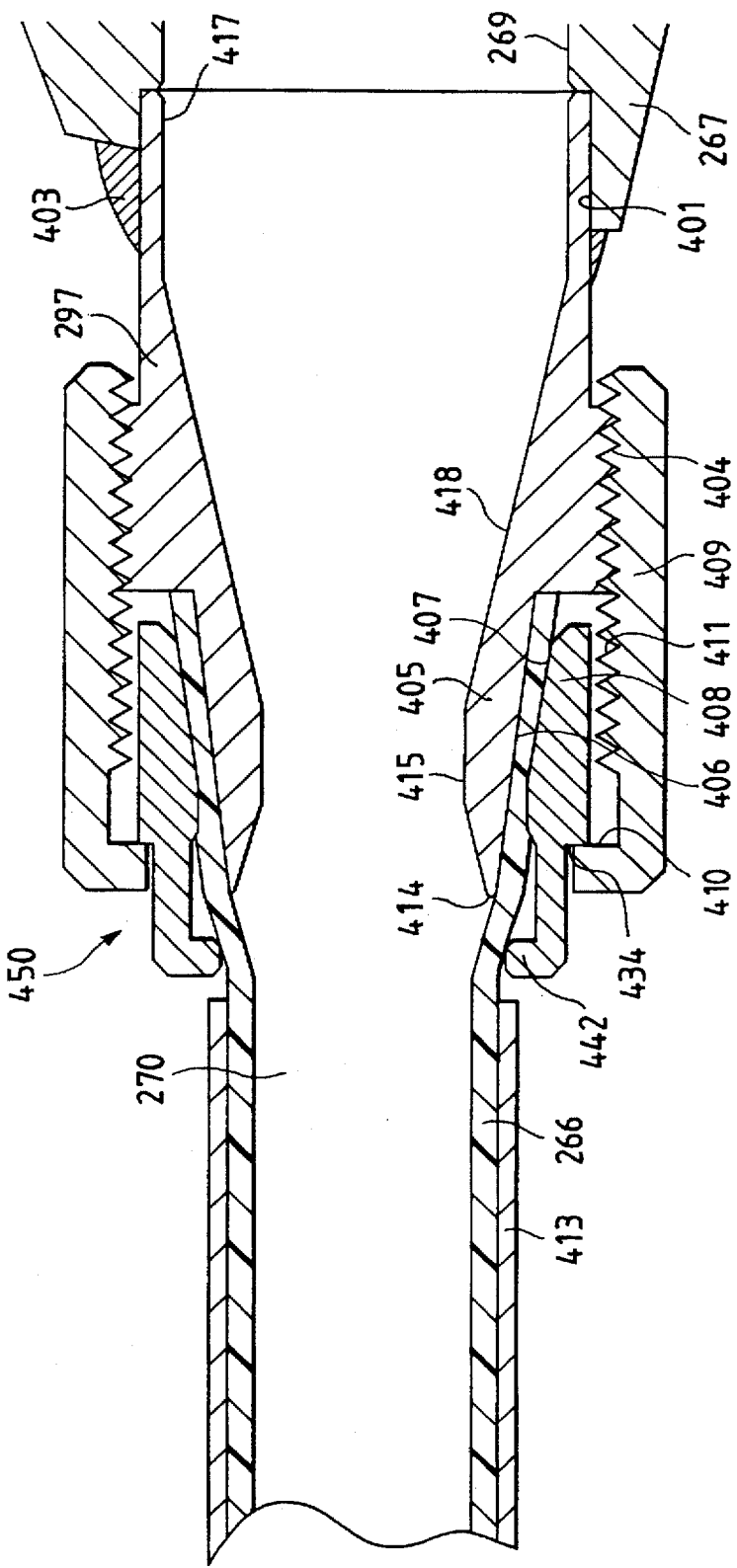
FIG. 12 shows the construction of the neighborhood of a tube connector 450 according to an eighth embodiment of the present invention.

FIG. 12 shows the construction of the neighborhood of a tube connector 450 according to an eighth embodiment of the present invention. The eighth embodiment is the same as the sixth embodiment, only except that the flange 436 of the clamping member 409 of the sixth embodiment is replaced with a flange 442 formed at the end of the retainer 408.

As with the sixth embodiment, the inside diameter of the flange 442 is smaller than the outside diameter of the flexible tube 266 fitted over the front end 414 of the channel socket 297, and hence the flange 442 presses the flexible tube 266 against the front end 414, thereby preventing the movement of the flexible tube. In other words, the internal circumference of the flexible tube 266 is connected to the front end 414 without a gap between them. Since the connector of the eighth embodiment is identical with that of the sixth embodiment in other respects, their explanation will be omitted here.

The method of putting together the flexible tube 266 and the channel socket 297 will now be described.

As with the sixth embodiment, the flexible tube 266 is cut to such a length that it can be fixed to the channel socket 297.

Subsequently, the cut end of the flexible tube 266 is guided to pass through the protecting member 413, the clamping member 409, and the retainer 408, in that order. The end of the flexible tube 266 is molded into a shape which facilitates the insertion of the mating section 405 of the channel socket 297 into the tube using a molding jig (not shown); namely, the end of the flexible tube is flared upon heat. In the molding process, the portion of the flexible tube 266 which is to be fitted over the front end 414 of the mating section 405 is prevented from being flared, thereby ensuring the prevention of creation of a gap between the flexible tube 266 and the front end 414 of the mating section 405 when the flexible tube and the channel socket are assembled into a unit.

After the flexible tube 266 has been fitted over the first tapered section 406 of the mating section 405, the retainer 408 is pressed to secure the flexible tube in position as a result of the clamping member 409 being engaged with the channel socket 297. In this event, the external peripheral surface of the flexible tube 266 is pressed by the inner periphery of the flange 442 of the retainer 408 such that the diameter of the flexible tube becomes smaller. The flexible tube 226 is pressed against the front end 414, so that the flexible tube is secured. As a result, it is possible to prevent a gap which would otherwise collect from being created between the flexible tube 266 and the front end 414. Next, the protecting member 413 is withdrawn to a predetermined location and is subjected to a heat shrinking operation, whereby the flexible tube 266 is fixedly sheathed with the protecting member.

In the joint assembly consisting of the flexible tube 266 and the channel socket 297 of the bifurcated tube body 267, the external thread 404 of the channel socket 297 is screwed into the internal thread 411 of the clamping member 409. As a result, the second tapered section 407 of the retainer 408 presses the outer periphery of the rear end of the flexible tube 266 fitted over the first tapered section 406 of the channel bracket 297, so that the flexible tube is secured. At the same time, the flange 442 of the retainer 408 presses the flexible tube 266 against the front end 414, whereby the flexible tube 266 is pressed against the thick portion of the mating section distant from the front end 414 of the first tapered section 406 of the channel socket 297. As a result, the high rigidity of the flexible tube is ensured. Further, if the medical instrument, and the like, exerts a force on the flexible tube 266, no gaps which would otherwise collect dirt are created between the flexible tube 266 and the front end 414. For this reason, the superior cleansing property of the joint is attained.

Figure 13:
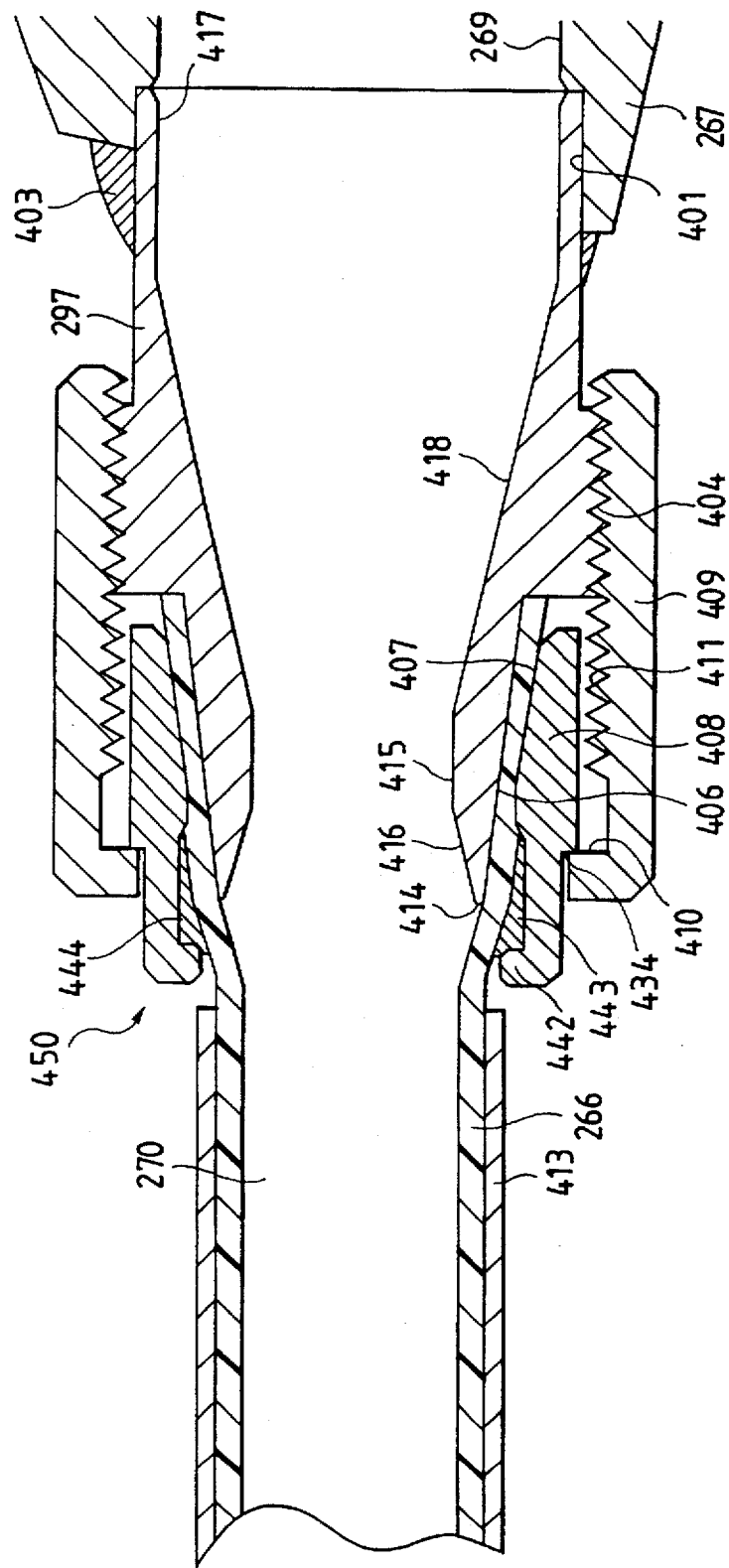
FIG. 13 shows the construction of the neighborhood of a tube connector according to a ninth embodiment of the present invention.
Figure 14:
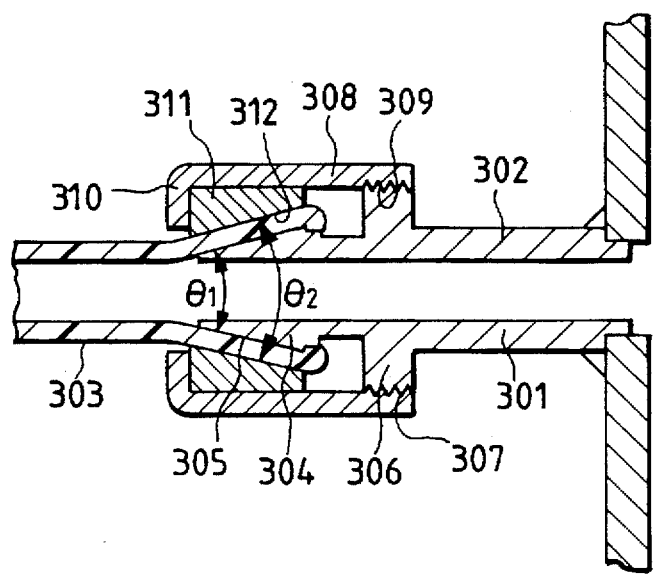
FIG. 14 is a sectional view of a connecting device for fixing the flexible tube to an endoscope according to a conventional art method.

FIG. 13 shows the construction of the neighborhood of a tube connector 450 according to a ninth embodiment of the present invention. The ninth embodiment is the same as the eighth embodiment only except for a difference with regard to the inside diameter of the flange 442 of the retainer 408. The inside diameter of the flange 442 is larger than the outside diameter of the flexible tube 266 fitted over the front end 414 of the channel socket 297, and hence the flange 442 does not press the flexible tube 266. However, a space 443 formed between the flange 442 and the outside diameter of the flexible tube 266 is filled with an adhesive 444.

The adhesive 444 prevents the portion of the flexible tube 226 fitted over the front end 414 of the channel socket 297 from moving. Since the connector of the ninth embodiment is identical with that of the eighth embodiment in other respects, their explanation will be omitted here.

The method of putting together the flexible tube 266 and the channel socket 297 will now be described.

As with the sixth embodiment, the flexible tube 266 is cut to such a length that it can be fixed to the channel socket 297. Subsequently, the cut end of the flexible tube 266 is guided to pass through the protecting member 413, the clamping member 409, and the retainer 408, in that order. The end of the flexible tube 266 is molded into a shape which facilitates the insertion of the mating section 405 of the channel socket 297 into the tube using a molding jig (not shown); namely, the end of the flexible tube is flared upon heat.

In the molding process, the portion of the flexible tube 266 which is to be fitted over the front end 414 of the mating section 405 is prevented from being flared, thereby ensuring the prevention of creation of a gap between the flexible tube 266 and the front end 414 of the mating section 405 when the flexible tube and the channel socket are assembled into a unit. After the flexible tube 266 has been fitted over the first tapered section 406 of the mating section 405, the retainer 408 is pressed to secure the flexible tube in position as a result of the clamping member 409 being engaged with the channel socket 297.

In this event, the external peripheral surface of the flexible tube 266 is not pressed by the inner periphery of the flange 442 of the retainer 408. The space 443 formed between the flange 442 and the outer periphery of the flexible tube 266 is filled with the adhesive 444. As a result, the portion of the flexible tube 226 positioned in the neighborhood of the front end 414 is prevented from moving, which in turn prevents the creation of a gap which would otherwise collect dirt between the flexible tube 266 and the front end 414. Next, the protecting member 413 is withdrawn to a predetermined location and is subjected to a heat shrinking operation, whereby the flexible tube 266 is fixedly sheathed with the protecting member.

In the joint assembly consisting of the flexible tube 266 and the channel socket 297 of the bifurcated tube body 267, the external thread 404 of the channel socket 297 is screwed into the internal thread 411 of the clamping member 409. As a result, the second tapered section 407 of the retainer 408 presses the outer periphery of the rear end of the flexible tube 266 fitted over the first tapered section 406 of the channel bracket 297, so that the flexible tube is secured. At the same time, as a result of the space 443 being filled with the adhesive 444, the flexible tube 226 is firmly pressed against the thick portion of the mating section away from the front end 414 of the first tapered section 406 of the channel socket 297, thereby the high rigidity of the flexible tube being ensured. Further, if the medical instrument, and the like, exerts a force on the flexible tube 266, no gaps which would otherwise collect dirt will be created between the flexible tube 266 and the front end 414. For this reason, the superior cleansing property of the joint is attained.

Moreover, no force acts on the portion of the flexible tube 266 fitted over the front end 414 of the channel socket 297, and therefore the strength of the flexible tube 266 is maintained.

Notes:

As will be understood from the foregoing discussion, the present invention can be embodied in various manners to provide the endoscopes recited in the following notes.

1. An endoscope having a conduit-providing flexible tube and a device for connecting said flexible tube, said device comprising a coupling member that is provided on the outer circumference with a first tapered portion the outside diameter of which decreases toward at least one end of said coupling member and that has a conduit in the interior, an annular retaining member that is fitted over the outer circumference of one end of said flexible tube which is to be fitted over said first tapered portion and that has on the inner circumference a second tapered portion the inside diameter of which decreases toward said at least one end in such a way as to provide engagement with said first tapered portion, and a clamp member that depresses said retaining member in the axial direction in which said first tapered portion flares, thereby depressing said flexible tube to be secured to said coupling member, characterized by further having an urging and covering that not only covers the outer circumferential portion of said flexible tube that has been fitted into said coupling member at the end portion coupled to said flexible tube but also urges said flexible tube to be secured to said first tapered portion.

In the endoscope recited in Note 1, the flexible tube is fitted over the first tapered portion on the outer circumference of the coupling portion the outside diameter of which tapered portion decreases toward at least one end and the outer circumference of this flexible tube is clamped by means of the clamp member so that it is secured to the coupling member. In addition, the inner circumference of the flexible tube is urged against the first tapered surface by means of the urging and covering member. These features ensure against the creation of filth-collecting gaps at the interface between the flexible tube and the first tapered surface.

In order to connect the flexible tube with the coupling member such as a channel or suction socket on a bifurcate tube, the flexible tube is sipped over one end portion of the coupling member and then fixed by depressing the urging and covering member such as a heat shrinking tube or a spiral tube against the flexible tube. In this way, the flexible tube is depressed onto the thick-walled part of the first tapered portion of the coupling member which is distant from the front end of the taper and this not only imparts rigidity but also enables the cleaning operation to be performed with better efficiency in the absence of any filth-collecting gaps on the inner circumference of the joint between the flexible tube and the coupling member.

2. An endoscope as recited in Note 1, wherein the end of said coupling member which has said first tapered portion and which is coupled to said flexible tube is located the closer to the coupling end of the flexible tube than the small-diameter end of a second tapered portion of said retainer member which has been fitted over the outer circumference of an end portion of said flexible tube fitted over said first tapered portion.

In the endoscope recited in Note 2, the end of said coupling member which has said first tapered portion and which is coupled to said flexible tube is located the closer to the coupling end of the flexible tube than the small-diameter end of a second tapered portion of said retainer member which has been fitted over the outer circumference of an end portion of said flexible tube fitted over said first tapered portion. This feature offers the advantage that when the operator is securing the flexible tube by means of said clamp member, he can check his operation visually by looking at an end portion of the flexible tube which has been fitted over said coupling member.

3. An endoscope as recited in Note 1, wherein the end of said first tapered portion of said coupling member which is on the side where it is to be coupled to said flexible tube has an outside diameter either substantial equal to or greater than the inside diameter of said flexible tube, with the difference being no more than 0.6 mm.

In the endoscope recited in Note 3, the outside diameter at the coupling end of the first tapered portion of the coupling member such as a channel or suction socket is either equal to or greater than the inside diameter of the flexible tube to be fitted to said coupling end, with the difference being no more than 0.6 mm. Because of this dimensional feature, the flexible tube is firmly depressed by means of the end portion of the coupling member which is on the side where it is coupled to said flexible tube such as to ensure against the creation of filth-collecting gaps at the interface between the flexible tube and the first tapered surface. Hence, the interior of the endoscope can be cleaned with higher efficiency.

4. An endoscope as recited in any one of Notes 1, 2 and 3, wherein the end of said first tapered portion of said coupling member which is on the side where it is to be coupled to said flexible tube has an outside diameter differing by no more than 0.1 mm from the inside diameter of the conduit in said coupling member at said end of said first tapered portion.

In the endoscope recited in Note 4, the difference between the outside and inside diameters of said coupling member at the end which is to be coupled to the flexible tube is adjusted to be no more than 0.1 mm and this dimensional feature ensures that the flexible tube can be connected to the coupling member with little formation of steps on the inner circumference of the joint between the flexible tube and the coupling member. Therefore, the two members can be joined together without creating any filth-collecting gaps on the inner circumference of the joint and its interior can be cleaned with improved efficiency since the cleaning brush will contact the interior evenly to shorten the time of cleaning under running water.

5. An endoscope as recited in any one of Notes 1–4, wherein said coupling member is provided with a third tapered surface that causes the inside diameter of the conduit to decrease from the end to which said flexible tube is to be connected towards the other end, said third tapered surface providing an angle of no more than 10 degrees with the axial direction.

In the endoscope recited in Note 5, the inner circumference of said coupling member is provided with a third tapered surface that causes the inside diameter of the conduit to decrease from the end to which the flexible tube is to be connected towards the other end, with the taper being no more than 10 degrees. This feature substantially eliminates the possibility of the formation of steps on the inner circumference of the joint between the coupling member and the flexible tube when they have been connected together. Thus, the smallest channel diameter is insured and yet the formation of steps on the inner circumference of the joint can be minimized.

6. An endoscope as recited in Note 1, wherein said urging and covering member is a heat shrinking tube made of a heat shrinkable material selected from among FEP, TFE, PFA and silicone rubber.

In this endoscope recited in Note 6, a heat shrinking tube made of a thermally shrinkable material such as FEP, TFE, PFA or silicone rubber is used as the urging and covering member, which is urged against the flexible tube which, in turn, is depressed with great force onto the first tapered surface of the coupling member. This ensures against the creation of filth-collecting gaps at the interface between the flexible tube and the first tapered surface, thereby enabling the interior of the endoscope to be cleaned with the higher efficiency.

The heat shrinking tube has the added advantage of preventing the buckling of the flexible tube; even if a bending force is exerted on the flexible tube, it can be prevented from buckling at the distal end of the coupling member such as a channel or suction socket. The heat shrinking tube is also capable of preventing the creation of filth-collecting gaps at the joint between the flexible tube and the coupling member.

7. An endoscope as recited in Note 1, wherein said urging and covering member is a spiral tube which, when it is not urged, has a smaller inside diameter than the outside diameter of the end of said coupling member on the side where it is to be coupled to the flexible tube.

In the endoscope recited in Note 7, a spiral tube which, when it is not urged, has a smaller diameter than the outside diameter of the end of the coupling member on the side where it is to be coupled to the flexible tube is used as the urging and covering member, which is urged against the flexible tube which, in turn, is depressed with great force to the first tapered surface of the coupling member. This also ensures against the creation of filth-collecting gaps at the interface between the flexible tube and the first tapered surface, thereby enabling the interior of the joint between the flexible tube and the coupling member to be cleaned with higher efficiency.

The spiral tube also serves as a protective member for the flexible tube and this contributes to the reduction in the number of parts to be assembled since the spiral tube need only be slipped over and fixed to an end of the coupling member.

8. An endoscope in which a channel held in position within the insertion section of the endoscope is connected to a bifurcate member in which said channel branches on the side closer to the operator into a plurality of conduits including one through which a medical instrument is to be inserted, which is positioned in a face-to-face relationship with a mounting hole open at the outer jacket of the endoscope and which communicates with the exterior via a medical instrument insertion passageway that penetrates through a tubular, medical instrument insertion socket member fitted into said mounting hole and that has the same inside diameter as said medical instrument insertion conduit, characterized in that said medical instrument insertion socket member is coupled to said bifurcate member by means of an urging connection cylinder that is fitted over said medical instrument insertion socket member and that has at one end a first connecting portion that is to be connected to said bifurcate member while having at the other end a second connecting portion that is provided with means for urging said medical instrument insertion socket member against said bifurcate member.

In the endoscope recited in Note 8, the urging connection cylinder fitted over the medical instrument insertion socket member is connected to the bifurcate member by means of the first connecting potion provided at one end of said urging connection cylinder whereas the urging means in the second connecting portion provided at the other end urges said insertion socket member against said bifurcate member, whereby these two members are brought into abutment and fixed relative to each other. In this way, the medical instrument insertion passageway through the insertion socket member and the medical instrument insertion conduit branching from the bifurcate member can be connected to each other without forming any steps at the joint or creating any filth-collecting gaps on the inner circumference of the joint.

As a result, the interior of the joint can be cleaned with improved efficiency since the cleaning brush will contact the interior evenly to shorten the time of cleaning under running water. If desired, the mounting hole may be provided in the grip portion of the insertion section of the endoscope and this grip portion may be molded of a resin without providing any thread portion; this offers the advantage of maintaining high strength for the grip portion.

9. An endoscope as recited in Note 8, wherein an elastic member substantially equal in diameter to said medical instrument insertion passageway and conduit is interposed at the boundary between said passageway and conduit.

In the endoscope recited in Note 9, said urging means depresses the elastic member provided at the boundary between said medical instrument insertion passageway and conduit, whereby the medical instrument insertion passageway through the medical instrument insertion socket member and the medical instrument insertion conduit branching from the bifurcate member can be connected to each other without forming any steps at the joint or creating any filth-collecting gaps on the inner circumference of the joint.

10. An endoscope as recited in Note 8, wherein anti-rotation means is provided in the area where said medical instrument insertion socket member is coupled to said bifurcate member.

In the endoscope recited in Note 10, anti-rotation means is provided in the area where said medical instrument insertion socket member is coupled to said bifurcate member and this ensures against rotation of said insertion socket member.

The anti-rotation means may comprise a plurality of anti-rotation projections that are provided on the outer circumference of the coupling side of the insertion socket member and which engage corresponding chambered portions provided in the bifurcate member and the combination of said anti-rotation projections and corresponding chambered portions ensures the provision of a rugged anti-rotation mechanism.

11. An endoscope having a connecting portion by which a metallic pipe member is connected to a second metallic member having a conduit of a diameter substantially equal to the inside diameter of said pipe member, said two metallic members being fitted together to have a generally abutting relationship, characterized in that a projection having formed therein a mounting hole of an inside diameter capable of sung fitting over the outside diameter of said pipe member is provided on said second metallic member coaxially with the conduit therein and that a cutout is formed in at least one area of said projection in the axial direction over a length substantially equal to the length over which said two metallic members are fitted together, with said two metallic members being secured by a fixing material that is applied to at least the area in which they are fitted together to have an abutting relationship.

In the endoscope recited in Note 11, the projection on said second metallic member can be secured to the mating surface of said pipe member by means of the fixing material which will readily flow into areas of limited access by way of the cutout which is of substantially the same length as the length over which the two metallic members are fitted together. Therefore, the applied fixing material will form a layer on the inner circumference of the joint between the two metallic members that can effectively connect the conduit in the pipe member to that in the second metallic member without forming any steps at the joint, nor creating any filth-collecting gaps on the inner circumference of the joint. As a result, the interior of the joint can be cleaned with improved efficiency since the cleaning brush will contact the interior evenly to shorten the time of cleaning such as under running water. The fixing material has the added advantage that it can form a reinforcement layer in the cutout to provide a thickness comparable to the thick-walled part of the projection on the second metallic member.

12. An endoscope as recited in Note 11, wherein said fixing material is colder.

In the endoscope recited in Note 11, the length over which the second metallic member such as a channel socket is to be inserted into the bifurcate tube and the length of the cutout are adjusted to be substantially identical in the area where the two conduits are connected by soldering and this increases the area over which the soldering iron can be applied, thereby allowing the applied solder to flow not only into the cutout but also the other areas so as to form a solder layer over the entire part of the mating surfaces. As a result, the two metallic members can be jointed together without creating any filth-collecting gaps on the inner circumference of the joint and this contributes to better efficiency in the cleaning operation. In addition, the use of solder in the connecting operation provides better efficiency than other fixing materials.

13. An endoscope having a connecting portion by which a metallic pipe is connected to a second metallic member having a conduit of a diameter substantially equal to the inside diameter of said pipe member, said two metallic members being fitted together to have a generally abutting relationship, characterized in that a layer of a fixing material which is thin enough to be substantially flush with the surface of the inner circumference of each of said pipe member and said second metallic member is formed in the mating area of said two members and the nearby area in such a way that said layer bridges the inner circumferences of the conduits in the two members.

In the endoscope recited in Note 13, a layer of a fixing material such as a brazing material or an adhesive which is substantially flush with the surface of the inner circumference of each of the pipe member and the second metallic member is provided in the mating area of said two members and the nearby area in such a way that said layer bridges the inner circumferences of the two members and this provision ensures against the creation of filth-collecting gaps at the joint between the conduits in the two metallic members. As a result, the interior of the joint can be cleaned with improved efficiency since the cleaning brush will contact the interior evenly to shorten the time of cleaning such as under running water.

14. An endoscope as recited in Note 13, wherein said fixing material is solder.

In the endoscope recited in Note 14, solder is used as the fixing material and this ensures against the creation of filth-collecting gaps at the joint of conduits. In addition, the use of solder in the connecting operation provides better efficiency than other fixing materials.

15. An endoscope having an insertion section provided with a flexible tube portion and a manipulating section that is coupled to the side of said insertion section which is the closer to the operator and that is covered with an outer jacket member, said endoscope further having:

a socket member provided within the flexible tube portion in said insertion section on the side which is the closer to the operator;

an interior providing member that is fixed to said outer jacket member on said manipulating section and which is provided with a first engaging portion;

a connecting member that is detachably fixed relative to said socket member in said flexible tube portion and which is provided with a second engaging portion that engages said first engaging portion of said interior providing member; and an urging member that urges either said connecting member or said interior providing member or both such that the engaging portions of said connecting member and said interior providing member are brought into intimate contact with each other, thereby fixing them together.

In the endoscope recited in Note 15, said connecting member is detachably fixed relative to the socket member on the side of said flexible tube portion which is the closer to the operator and said urging member works in such a way that the engaging portions of said connecting member and said interior providing member are brought into intimate contact with each other in order to assure positive engagement of said two members. If necessary, the urging force of said urging member may be removed such that the connecting member can be replaced by being detached from the interior providing member.

In the endoscope recited in Note 15, the socket member such as cylindrical member in the flexible tube portion on the side which is the closer to the operator is connected to the interior providing member with the intermediary of the connecting member and by removing screws or other means that secure the connecting member to said socket member, the latter can be removed as required. The endoscope has the additional advantage that if a ring for fixing the insertion section which is used as the urging member is tightened with an excessive urging force such as torque during reassembly, the connecting member is the only part that will be broken and one does not need to replace any other parts, which contributes to a reduction in the number of steps required in disassembling and reassembling operations.

16. An endoscope as recited in Note 15, wherein said connecting member has a cutout provided along its entire length in the axial direction of the insertion section and which has a greater width than the thickest member incorporated in the endoscope.

On account of the cutout provided in the connecting member, even the widest member to be incorporated in the endoscope recited in Note 16 can be easily inserted into said connecting member and all the members incorporated in the endoscope can be removed and replaced in a direction normal to the axis of the insertion section of the endoscope, and this also contributes to a reduction in the number of steps involved in the disassembling and reassembling operations.

17. An endoscope having an insertion section provided with a flexible tube portion and a manipulating section that is coupled to the side of said insertion section which is the closer to the operator and that is covered with an outer jacket member, said endoscope further having:

a socket member provided within the flexible tube portion in said insertion section on the side which is the closer to the operator;

an interior providing member that is fixed to said outer jacket member on said manipulating section; and connecting means by which said interior providing member and said socket member are coupled in such a way that they are pivotal relative to each other in the axial direction of the insertion section.

In the endoscope recited in Note 17, the socket member on the side of the flexible tube in the insertion section which is the closer to the operator is connected via the connecting means to the interior providing member fixed to the outer jacket member on the manipulating section and said connecting means ensures that the interior providing member in said manipulating section and said socket member are capable of pivoting in the axial direction of the insertion section.

This arrangement offers the advantage that even if the insertion section of the endoscope is inserted into a cavity in patient's body to such a depth that the length of insertion almost reaches the area where it is coupled to the manipulating section, said area of coupling between the insertion and manipulating sections will pivot and bend to curve under an exerted force without causing any discomfort to the patient.

18. An endoscope as recited in Note 17, wherein said connecting means has at least two engaging pins and a connection cylinder coupled to said interior providing member, said engaging pins being detachably fixed to said socket member and provided in such a way that they have their heads protrude when mounted and said connection cylinder having a greater inside diameter than the outside diameter of said socket member and being provided in the sidewall with a hole into which at least one of the heads of said engaging pins can be loosely fitted.

In the endoscope recited in Note 18, the socket member on the side of the insertion section which is the closer to the operator is coupled via the connection cylinder to the interior providing member in the manipulating section and the connection cylinder has a clearance from the socket member, with at least one of the engaging pins being loosely fitted into the hole made in said connection cylinder. Because of this arrangement, both the socket member and the interior providing member are capable of pivoting.

The resulting advantage is that even if the insertion section of the endoscope is inserted into a cavity in a patient's body to such a depth that the length of insertion almost reaches the area where it is coupled to the manipulating section, said area of coupling between the insertion and manipulating sections will pivot and bend to curve under an exerted force without causing any discomfort to the patient.

19. An endoscope as recited in Note 18, which is further provided with an anti-buckle socket member that covers the heads of said engaging pins.

The endoscope recited in Note 18 offers the advantage that even if the engaging pins loosen, the anti-buckle socket member covering their heads prevent them from slipping out completely and there is no possibility that the socket member will separate from the connection cylinder, which would otherwise cause the destruction of the parts or components incorporated in the conduit.

20. An endoscope as recited in Note 18, wherein one of the holes made in said connection cylinder is of substantially the same diameter as the heads of said engaging pins whereas the other hole is of a greater diameter than said heads.

In the endoscope recited in Note 20, the other of the holes made in the connection cylinder has a larger diameter than the heads of the engaging pins and this insures that both the interior providing member in said manipulating section and said socket member provided on the side of said insertion section which is the closer to the operator are capable of pivoting in the axial direction of the insertion section upon the engaging pin inserted into said one of the holes having substantially the same diameter as the heads of the engaging pins. If desired, one of the engaging pins such as screws can be inserted into the small-diameter hole by having a certain part, say the bottom, of its head snugly fitted into said hole and this ensures that the socket member and the connection cylinder are joined together in such a way that their positions are practically fixed in both the axial and radial directions of the insertion section; as a result, both members are capable of pivoting on the screw fitted into the small-diameter hole.

21. An endoscope in which a channel held in position within the insertion section of the endoscope is connected to a bifurcate member in which said channel branches on the side closer to the operator into a plurality of conduits including one through which a medical instrument is to be inserted, which is positioned in a face-to-face relationship with a mounting hole open at the outer jacket of the endoscope, which communicates with the exterior via a medial instrument insertion passageway that penetrates thorough a tubular, medical instrument insertion socket member fitted into said mounting hole and that has the same inside diameter as said medical instrument insertion conduit, characterized in that said bifurcate member is positioned slidable such that the position of said medical instrument insertion conduit can be varied relative to said mounting hole.

As described on the foregoing pages, the endoscope of the invention is such that the flexible tube is slipped over the first tapered portion which is an end portion of the coupling member and urged against said tapered portion by means of the urging and covering member. As a result, higher rigidity is ensured without causing any deformation and yet the flexible tube can positively be secured in position; in addition, connection of the flexible tube can be accomplished without creating any filth-collecting gaps on the inner circumference of the joint and this contributes to better efficiency in the cleaning operation.

What is claimed is:

1. An endoscope including:
   a tube body (267) which forms a conduit;
   a flexible tube (266) which forms a conduit so as to communicate with the conduit of the tube body when it is connected to the tube body; and
   a joint (450) for jointing together the tube body and the flexible tube, the joint comprising
   a coupling member (297) which is disposed between the tube body and the flexible tube and has a first tapered section (406) formed on the external surface thereof, so as to become gradually larger toward at least a first distal end of the coupling member, and the end of the flexible tube being fitted over the first tapered section, a ring-shaped retainer (408) fitted over the end of the flexible tube for fixing the end of the flexible tube around the coupling member, the ring-shaped retainer having a second tapered section (407), the second tapered section being formed on the internal peripheral surface of the retainer such that the diameter of the retainer becomes gradually larger so as to engage with the first tapered section of the coupling member, a clamping member (409) which fixes the flexible tube to the coupling member by pressing the retainer upon engagement with the coupling member, and a regulating member (436, 440, 442, or 444) for regulating relative movement between the flexible tube and the end of the coupling member in the vicinity of an area where the flexible tube is in contact with an end (414) of the coupling member.

2. The endoscope as defined in claim 1, wherein the regulating member restricts the radial movement of the flexible tube toward the outside.

3. The endoscope as defined in claim 1, wherein the regulating member is integral with the clamping member (409).

4. The endoscope as defined in claim 3, wherein the regulating member has a flange (436) formed on a first end of the clamping member, and the flange is positioned distant from the end of the coupling member fixed to the end of the flexible tube and has a smaller diameter than the outside diameter of an end (414) of the coupling member.

5. The endoscope as defined in claim 3, wherein the radial inner end of the flange presses the flexible tube.

6. The endoscope as defined in claim 1 or 3, wherein the regulating member has an adhesive filled into a space formed between the clamping member and the flexible member.

7. The endoscope as defined in claim 1, wherein the regulating member is integral with the retainer (408).

8. The endoscope as defined in claim 7, wherein the regulating member has a flange (442) formed at the end of the retainer, and the flange is positioned distant from the end of the coupling member fixed to the end of the flexible tube and has a smaller diameter than the outside diameter of the flexible tube fitted over the end (414) of the coupling member.

9. The endoscope as defined in claim 7, wherein the radial inner end of the flange presses the flexible tube.

10. The endoscope as defined in claim 7, wherein the regulating member has an adhesive filled into a space formed between the clamping member and the flexible member.

11. The endoscope as defined in claim 1, wherein the regulating member is an urging and covering member (112) disposed so as to be fitted over the flexible tube and to cover the end of the coupling member which is in contact with the flexible tube.

12. The endoscope as defined in claim 1, wherein the coupling member has a first end which has substantially the same diameter as the inside diameter of the flexible tube and is connected to the conduit, and a second end which has a diameter substantially the same as or larger than the inside diameter of the flexible tube and is connected to the flexible tube.

13. The endoscope as defined in claim 1, wherein the coupling member has a flange, and a thread (404) is formed on the external peripheral surface of the flange so as to engage with the clamping member.

14. The endoscope as defined in claim 12, wherein the second end of the coupling member projects beyond the retainer, and a third tapered section is formed on the internal peripheral surface of the second end.

15. The endoscope as defined in claim 14, wherein a difference between the outside diameter of the end (414) at the second end and the inside diameter of the same on the second end is less than 0.1 mm.

16. The endoscope as defined in claim 12, wherein a third tapered section (416) is formed on the inner peripheral surface of the second end of the coupling member in such a way that the inside diameter of the conduit becomes smaller from the edge of the second end being in contact with the flexible tube toward the other end of the coupling member.

17. The endoscope as defined in claim 16, wherein a cone angle of the third tapered section is less than 10°.

18. The endoscope as defined in claim 12 or 16, wherein a fourth tapered section (418) is formed between the first end and the second end of the coupling member in such a way that the inside diameter of the conduit becomes smaller from the first end toward the second end.

19. The endoscope as defined in claim 12, wherein a difference between the inside diameter of the flexible tube and the outside diameter of the edge of the second end is less than 0.6 mm.

20. The endoscope as defined in claim 11, wherein the urging and covering member is a coiled tube such as a tightly wound coil spring.

21. The endoscope as defined in claim 11, wherein the urging and covering member is a heat shrinkable tube.

22. The endoscope as defined in claim 11, wherein the urging and covering member is fitted between the coupling member and the flexible tube.

23. The endoscope as defined in claim 1, wherein the flexible tube is made from fluororesin.

24. The endoscope as defined in claim 1, wherein the conduit of the tube body is a path through which a forceps passes.

25. The endoscope as defined in claim 1, wherein the conduit is a passage used for aspiration.

26. The endoscope as defined in claim 1, wherein the portion of the coupling member, around which the flexible tube is fitted, is formed to a larger thickness.

27. The endoscope as defined in claim 18, wherein an interface between the third tapered section and the fourth tapered section forms the minimum inside diameter of the conduit.

28. The endoscope as defined in claim 1, further comprising a protecting member (413) for covering the flexible tube.

29. The endoscope as defined in claim 28, wherein the protecting member is a heat shrinkable tube.

* * * * *